US009265589B2

(12) United States Patent
Hartmann et al.

(10) Patent No.: US 9,265,589 B2
(45) Date of Patent: Feb. 23, 2016

(54) SYSTEM AND METHOD FOR NAVIGATED DRILL GUIDE

(75) Inventors: Steven L. Hartmann, Superior, CO (US); Joel S. Hughes, Erie, CO (US); Joseph Moctezuma, Golden, CO (US); Laurent Verard, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1398 days.

(21) Appl. No.: 11/935,793

(22) Filed: Nov. 6, 2007

(65) Prior Publication Data

US 2009/0118742 A1    May 7, 2009

(51) Int. Cl.
*A61B 5/05* (2006.01)
*A61B 19/00* (2006.01)
*A61B 17/17* (2006.01)

(52) U.S. Cl.
CPC .............. *A61B 19/52* (2013.01); *A61B 17/1703* (2013.01); *A61B 19/201* (2013.01); *A61B 19/5244* (2013.01); *A61B 2019/304* (2013.01); *A61B 2019/462* (2013.01); *A61B 2019/5483* (2013.01)

(58) Field of Classification Search
USPC .................... 600/424, 425, 426, 429; 606/80
See application file for complete search history.

(56) References Cited

U.S. PATENT DOCUMENTS

| | | |
|---|---|---|
| 4,642,786 A | 2/1987 | Hansen |
| 5,249,581 A | 10/1993 | Horbal et al. |
| 5,253,647 A | 10/1993 | Takahashi et al. |
| 5,318,025 A | 6/1994 | Dumoulin et al. |
| 5,353,795 A | 10/1994 | Souza et al. |
| 5,377,678 A | 1/1995 | Dumoulin et al. |
| 5,425,367 A | 6/1995 | Shapiro et al. |
| 5,515,264 A | 5/1996 | Stacey |
| 5,592,939 A | 1/1997 | Martinelli |

(Continued)

FOREIGN PATENT DOCUMENTS

| | | |
|---|---|---|
| EP | 0326768 A2 | 8/1989 |
| EP | 0930046 A2 | 7/1999 |

(Continued)

OTHER PUBLICATIONS

European Search Report mailed Jan. 18, 2005 for EP04024457 claiming benefit of U.S. Appl. No. 10/687,539, filed Oct. 16, 2003.

(Continued)

*Primary Examiner* — Christopher Cook
(74) *Attorney, Agent, or Firm* — Harness, Dickey

(57) ABSTRACT

A system for tracking a navigated instrument. The system can include a first elongated instrument and a second elongated instrument. The first elongated instrument can have a first proximal end and a first distal end. The first elongated instrument can be adapted to be positioned relative to an anatomy. The second elongated instrument can move adjacent to the first elongated instrument. The second elongated instrument can have a second proximal end and a second distal end. The system can also include at least one tracking device coupled to the second elongated instrument. When the second elongated instrument is in a first position, the at least one tracking device tracks the first distal end of the first elongated instrument, and when the second elongated instrument is in a second position, the at least one tracking device tracks the second distal end of the second elongated instrument.

23 Claims, 13 Drawing Sheets

(56) References Cited

U.S. PATENT DOCUMENTS

| | | | |
|---|---|---|---|
| 5,769,843 | A | 6/1998 | Abela et al. |
| 5,915,485 | A * | 6/1999 | McAtavey ................ 175/18 |
| 5,938,602 | A * | 8/1999 | Lloyd .................... 600/424 |
| 5,983,126 | A | 11/1999 | Wittkampf |
| 6,226,548 | B1 | 5/2001 | Foley et al. |
| 6,280,149 | B1 * | 8/2001 | Able et al. ................ 417/63 |
| 6,381,485 | B1 | 4/2002 | Hunter et al. |
| 6,447,504 | B1 | 9/2002 | Ben-Haim et al. |
| 6,470,207 | B1 | 10/2002 | Simon et al. |
| 6,474,341 | B1 | 11/2002 | Hunter et al. |
| 6,499,488 | B1 | 12/2002 | Hunter et al. |
| 6,530,929 | B1 | 3/2003 | Justis et al. |
| 6,701,179 | B1 | 3/2004 | Martinelli et al. |
| 7,152,608 | B2 | 12/2006 | Hunter et al. |
| 7,217,276 | B2 | 5/2007 | Henderson et al. |
| RE40,852 | E | 7/2009 | Martinelli et al. |
| 7,599,730 | B2 | 10/2009 | Hunter et al. |
| RE41,066 | E | 12/2009 | Martinelli et al. |
| 2001/0036245 | A1 | 11/2001 | Kienzle et al. |
| 2002/0016599 | A1 | 2/2002 | Kienzle et al. |
| 2002/0156363 | A1 | 10/2002 | Hunter et al. |
| 2003/0074011 | A1 | 4/2003 | Gilboa et al. |
| 2003/0187351 | A1 | 10/2003 | Franck et al. |
| 2003/0208122 | A1 * | 11/2003 | Melkent et al. .......... 600/426 |
| 2004/0097805 | A1 | 5/2004 | Verard et al. |
| 2004/0097806 | A1 | 5/2004 | Hunter et al. |
| 2005/0074304 | A1 | 4/2005 | Couture et al. |
| 2005/0085714 | A1 | 4/2005 | Foley et al. |
| 2005/0251186 | A1 * | 11/2005 | Revie et al. ............. 606/180 |
| 2006/0025677 | A1 * | 2/2006 | Verard et al. ............ 600/423 |
| 2006/0084867 | A1 | 4/2006 | Tremblay et al. |
| 2006/0278247 | A1 | 12/2006 | Hunter et al. |
| 2008/0200794 | A1 * | 8/2008 | Teichman et al. ........ 600/407 |
| 2009/0036768 | A1 * | 2/2009 | Seehusen et al. ......... 600/424 |

FOREIGN PATENT DOCUMENTS

| | | |
|---|---|---|
| WO | WO-0069335 A1 | 11/2000 |
| WO | WO-0187136 A2 | 11/2001 |

OTHER PUBLICATIONS

European Search Report mailed Sep. 29, 2004 for EP04016056 claiming benefit of U.S. Appl. No. 10/619,216, filed Jul. 14, 2003.

International Search Report and Written Opinion mailed Mar. 3, 2009 for PCT/US2008/082489 claiming benefit of U.S. Appl. No. 11/935,793 filed Nov. 16, 2007.

International Search Report for PCT/US96/10050 mailed Aug. 6, 1996 claiming priority to U.S. Appl. No. 08/490,342, filed Jun. 14, 1995.

International Search Report mailed Jan. 6, 2001 for PCT/US00/41559 claiming benefit of U.S. Appl. No. 09/428,722, filed Oct. 28, 1999.

Partial European Search Report mailed Mar. 1, 2004 for EP03024327 claiming benefit of U.S. Appl. No. 10/299,969, filed Nov. 19, 2002.

Schreiner, S., et al: "An Ultrasonic Approach to Localization of Fiducial Markers for Interactive, Image-Guided Neurosurgery—Part II: Implementation and Automation" IEEE Transactions on Biomedical Enginerring, US, IEEE, Inc. New York, vol. 45, No. 5, May 1, 1998, pp. 631-641, XP000740789; ISSN: 0018-9294, the whole document.

* cited by examiner

SYSTEM AND METHOD FOR NAVIGATED DRILL GUIDE

FIELD

The present disclosure relates generally to navigated surgery, and more specifically, to systems and methods for a navigated drill guide.

BACKGROUND

The statements in this section merely provide background information related to the present disclosure and may not constitute prior art.

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in navigated medical procedures.

Generally, during a navigated procedure, images are acquired by a suitable imaging device for later display on a workstation. The navigation system tracks the patient, instruments and other devices in the surgical field or patient space. These tracked devices are then displayed relative to the image data on the workstation in image space. In order to track the patient, instruments and other devices, the patient, instruments and other devices can be equipped with tracking devices.

Generally, tracking devices are coupled to an exterior surface of the instrument, and can provide the surgeon, via the tracking system, an accurate depiction of the location of that instrument in the patient space. In cases where a first instrument moves within a second instrument, however, it can be difficult to accurately determine the location of the distal most end of the instrument assembly, as depending upon the movement of the first instrument within the second instrument, either the first instrument or the second instrument can form the distal most end. For example, in the case of a drill bit that moves within a drill guide, depending upon the advancement of the drill bit, the end of the drill guide or the end of the drill bit can form the distal most end of the instrument assembly.

SUMMARY

A system for tracking a navigated instrument. The system can include a first elongated instrument and a second elongated instrument. The first elongated instrument can have a first proximal end and a first distal end. The first elongated instrument can be adapted to be positioned relative to an anatomy. The second elongated instrument can move adjacent to the first elongated instrument. The second elongated instrument can have a second proximal end and a second distal end. The system can also include at least one tracking device coupled to the second elongated instrument. When the second elongated instrument is in a first position, the at least one tracking device tracks the first distal end of the first elongated instrument, and when the second elongated instrument is in a second position, the at least one tracking device tracks the second distal end of the second elongated instrument.

Provided is a system for tracking a navigated instrument. The system can include a guide instrument. The guide instrument can have a first proximal end and a first distal end. The guide instrument can define a first bore that can be adapted to slideably receive an elongated instrument that has a second distal end. The guide instrument can be positionable adjacent to an anatomy. The system can also include at least one electromagnetic tracking device coupled to the elongated instrument. The at least one electromagnetic tracking device can be moveable relative to the guide instrument. When the elongated instrument is in a first position, the at least one electromagnetic tracking device tracks the first distal end of the guide instrument, and when the elongated instrument is in a second position, the at least one electromagnetic tracking device tracks the second distal end of the elongated instrument.

A method for tracking a navigated instrument. The method can include positioning a first elongated instrument relative to a second elongated instrument having a first proximal end and a first distal end, the second elongated instrument having a second proximal end and a second distal end. The method can also include positioning at least one tracking device on the second elongated instrument. The method can include moving the second elongated instrument that adjacent to the first elongated instrument. The method can further include tracking the at least one tracking device, and determining, based on the tracking of the at least one tracking device, a location of the first distal end of the first elongated instrument or the second distal end of the second elongated instrument.

Provided is a system for tracking a navigated instrument. The system can include a guide instrument. The guide instrument can have a first proximal end, a first distal end and can define a first bore that can be adapted to slideably receive an elongated instrument that has a second distal end. The guide instrument can be positionable adjacent to an anatomy. The system can also include at least one tracking device coupled about the elongated instrument. The at least one tracking device can be moveable relative to the guide instrument. When the elongated instrument is in a first position, the at least one tracking device can track the first distal end of the guide instrument, and when the elongated instrument is in a second position, the at least one tracking device can track the second distal end of the elongated instrument. The relative movement of the elongated instrument within the guide instrument can act to vary a signal induced in the at least one tracking device.

A method for tracking a navigated instrument is also provided. The method can include positioning a first elongated instrument relative to a second elongated instrument. The first elongated instrument can include a first proximal end and a first distal end, and the second elongated instrument can have a second proximal end and a second distal end. The method can further include positioning at least one tracking device on the second elongated instrument, and moving the second elongated instrument adjacent to the first elongated instrument to vary a signal induced in the at least one tracking device. The method can further include tracking the at least one tracking device, and determining, based on the tracking of the at least one tracking device, a location of the first distal end of the first elongated instrument or the second distal end of the second elongated instrument.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 1:
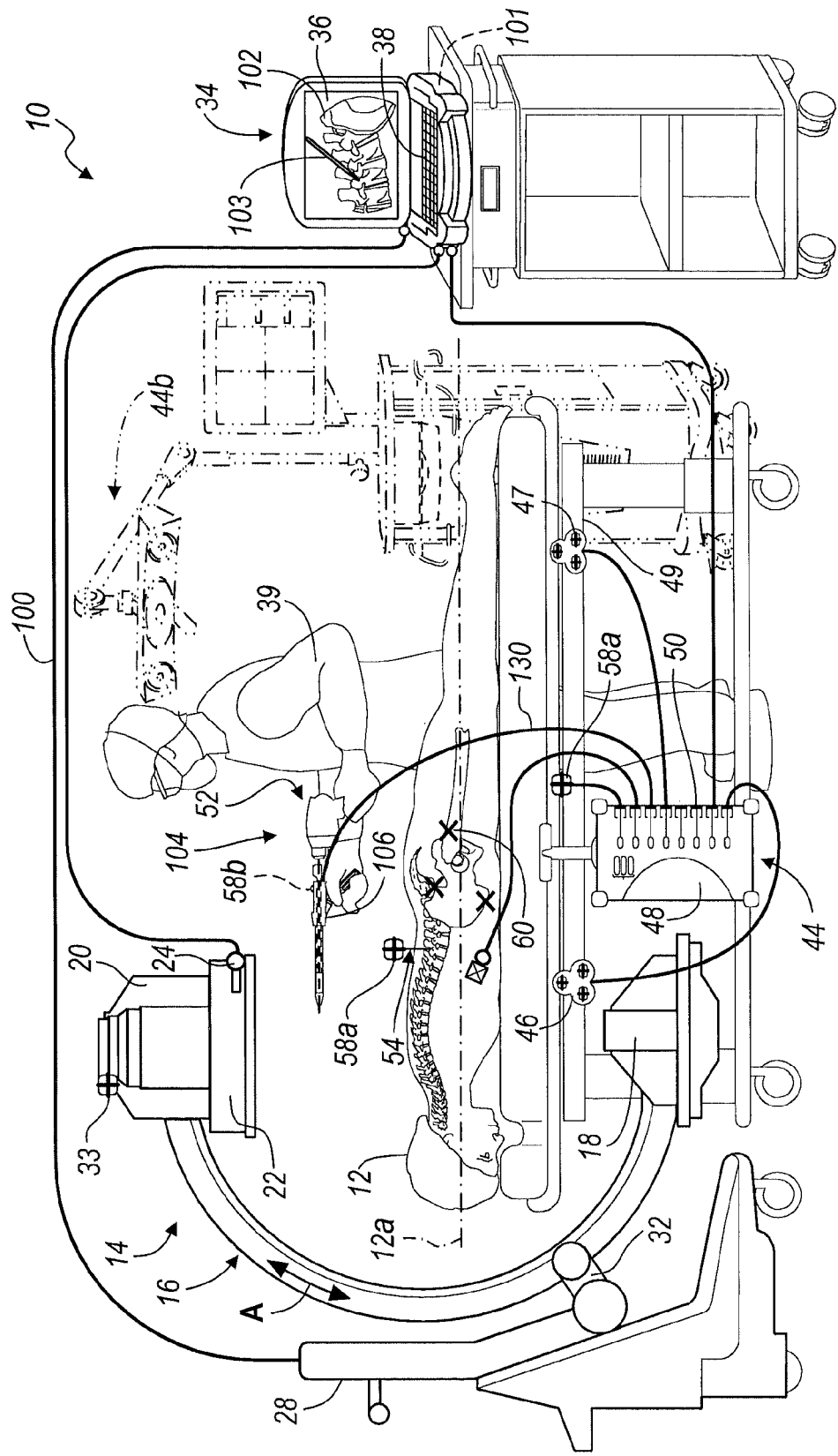
FIG. 1 is a diagram of a navigation system including a navigated drill guide according to various embodiments of the present disclosure.
Figure 3:
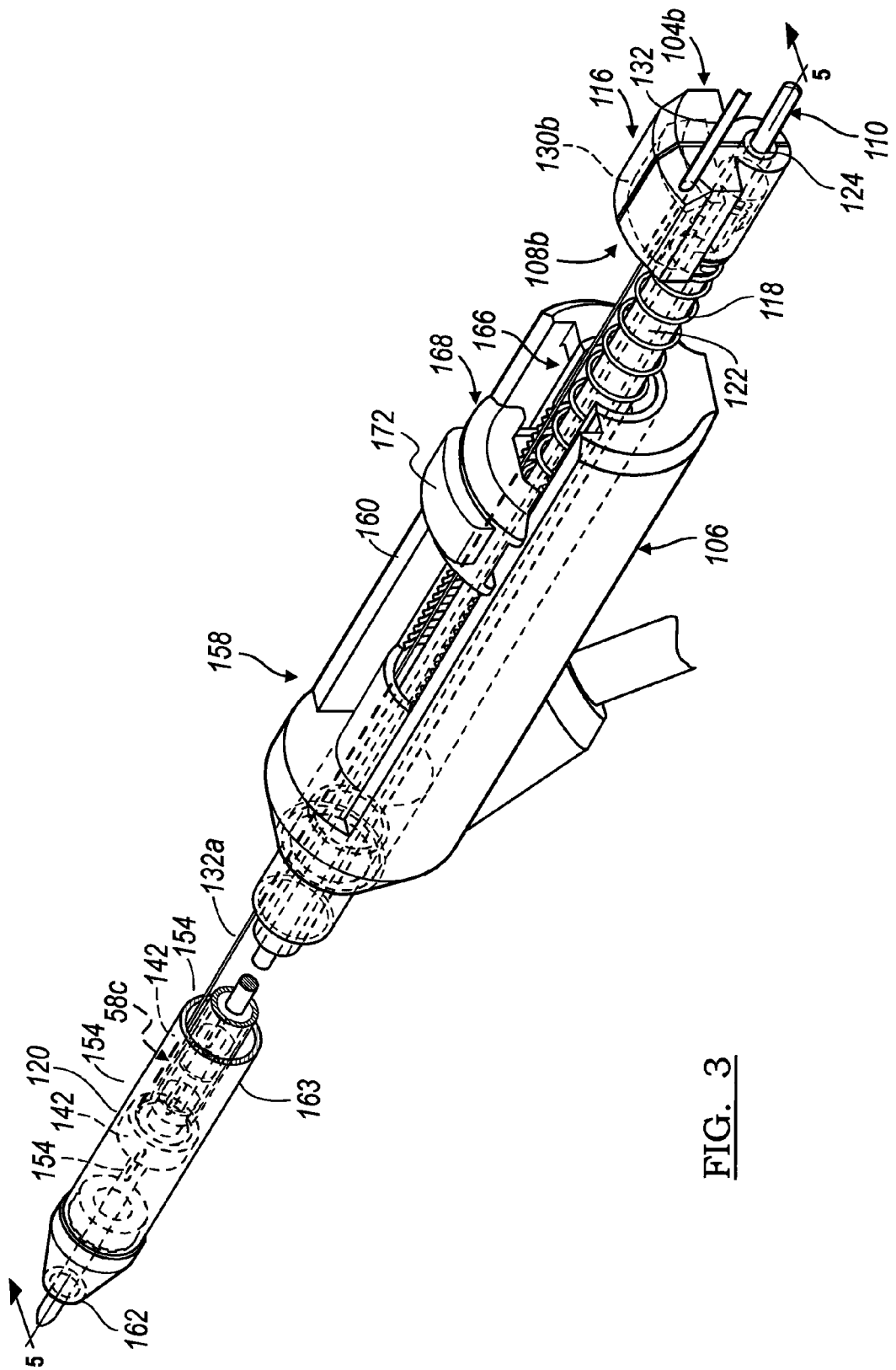
FIG. 3 is a perspective view of a navigated drill guide for use with the navigation system of FIG. 1.
Figure 5:
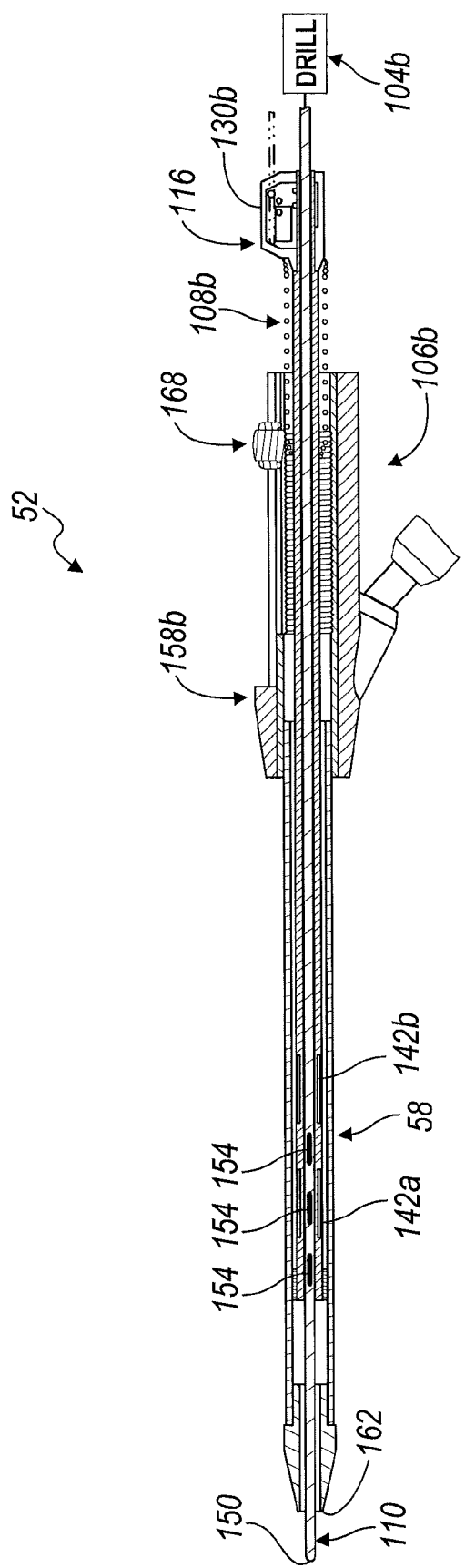
Figure 6:
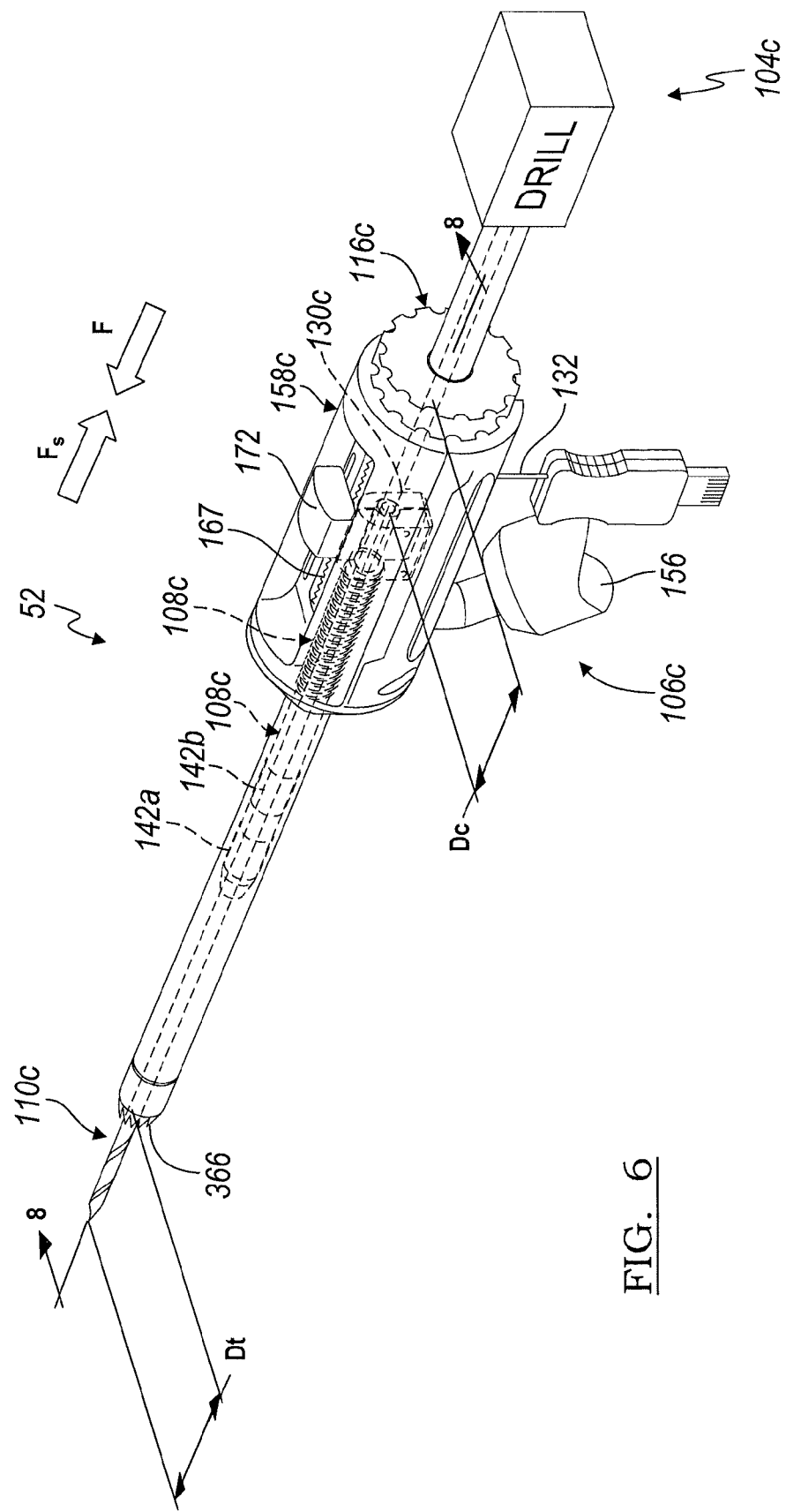
Figure 7:
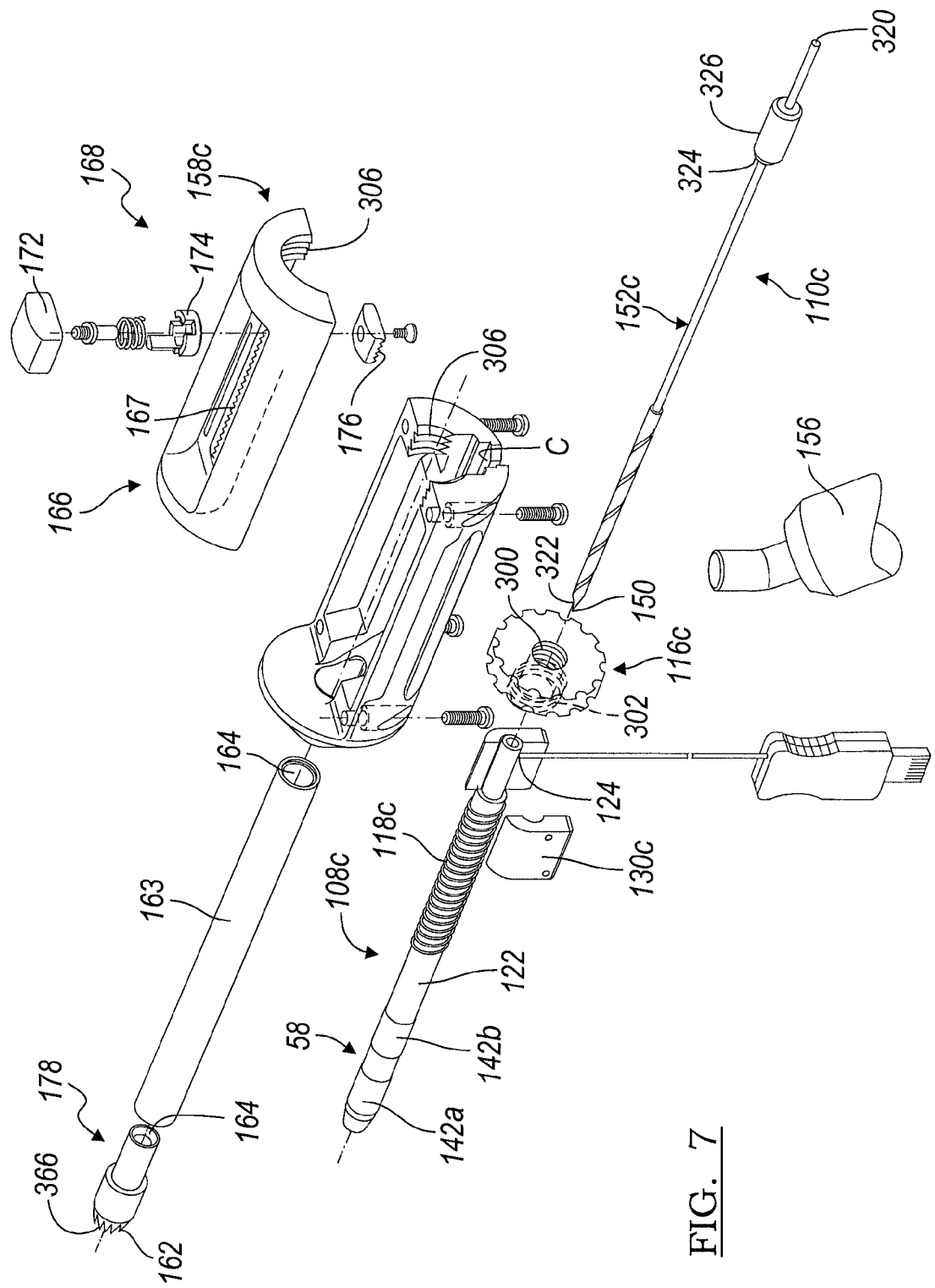
Figure 9:
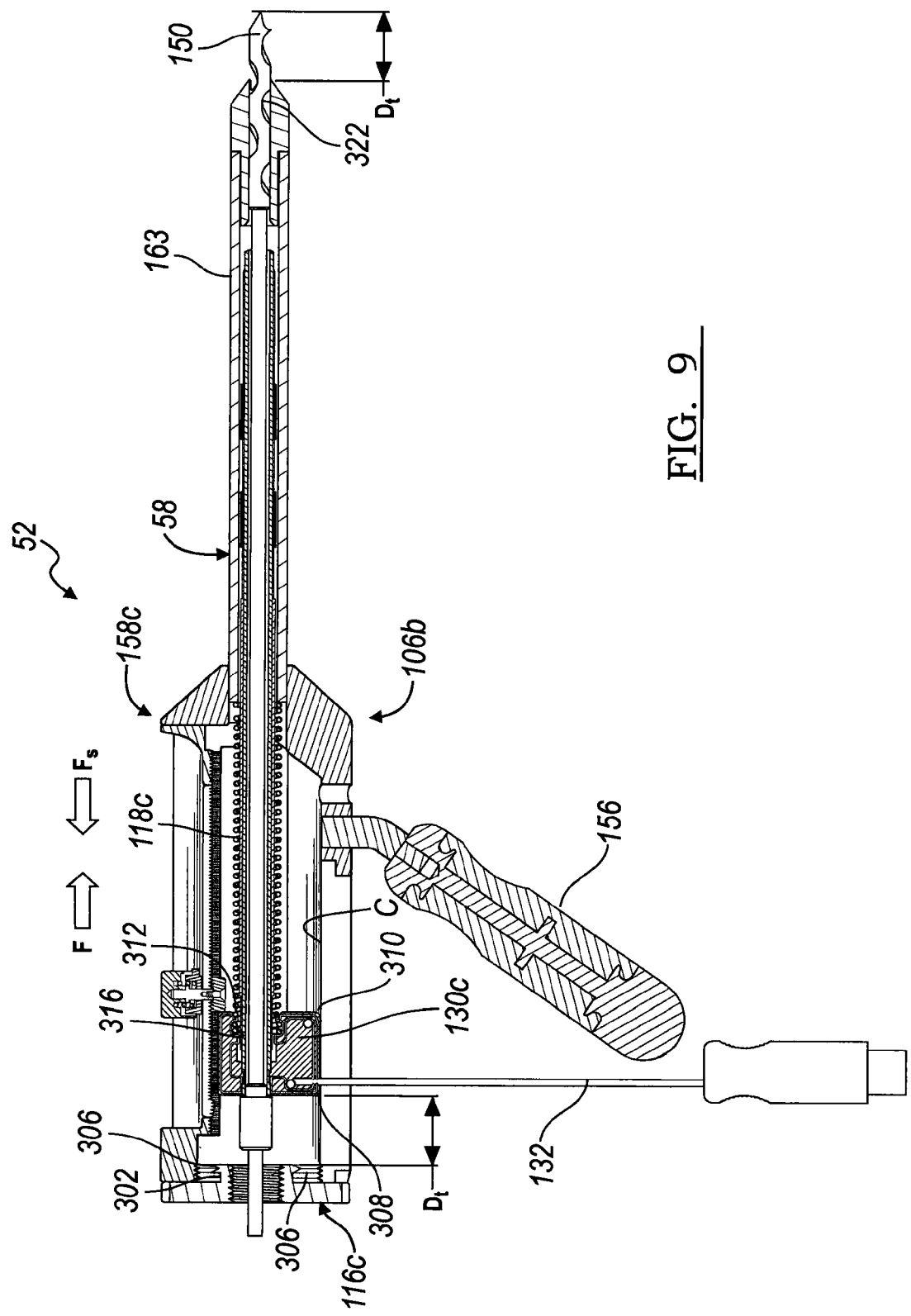
Figure 10:
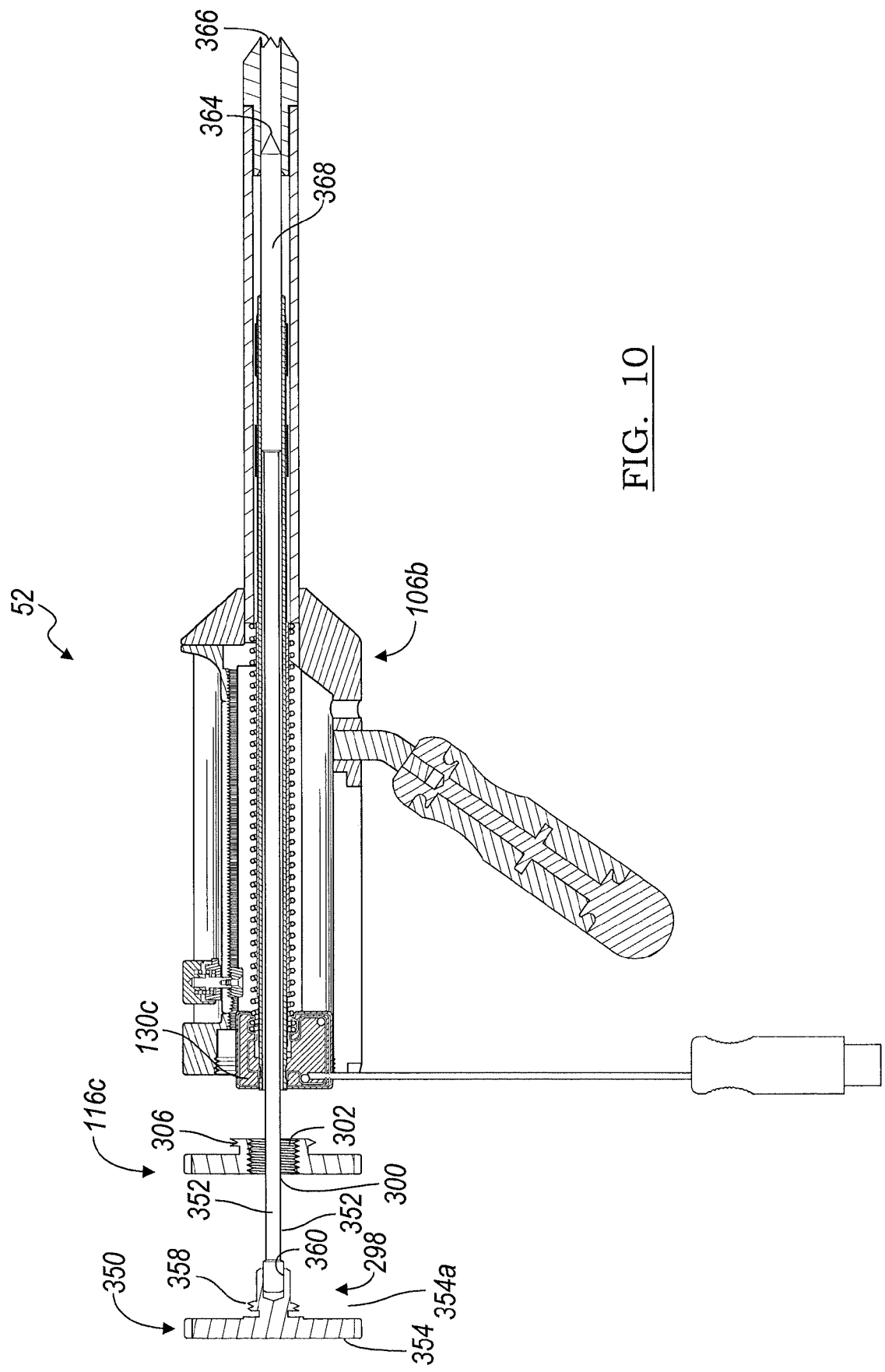
Figure 11:
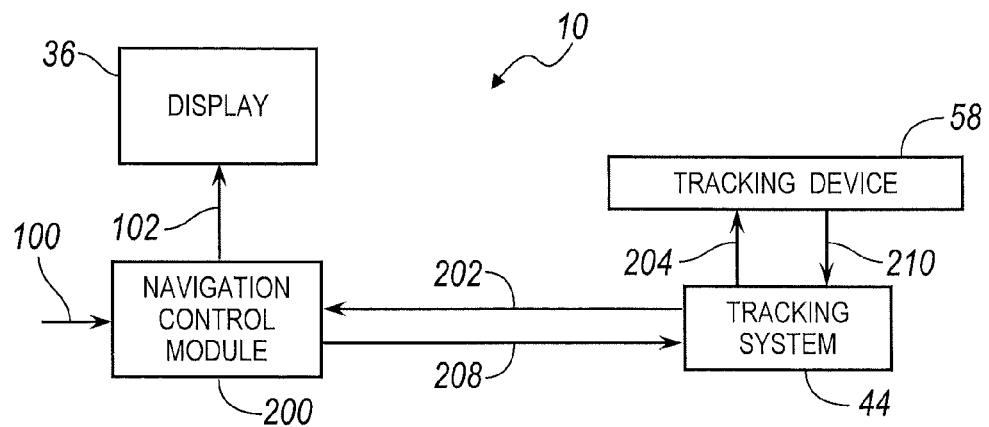
Figure 12:
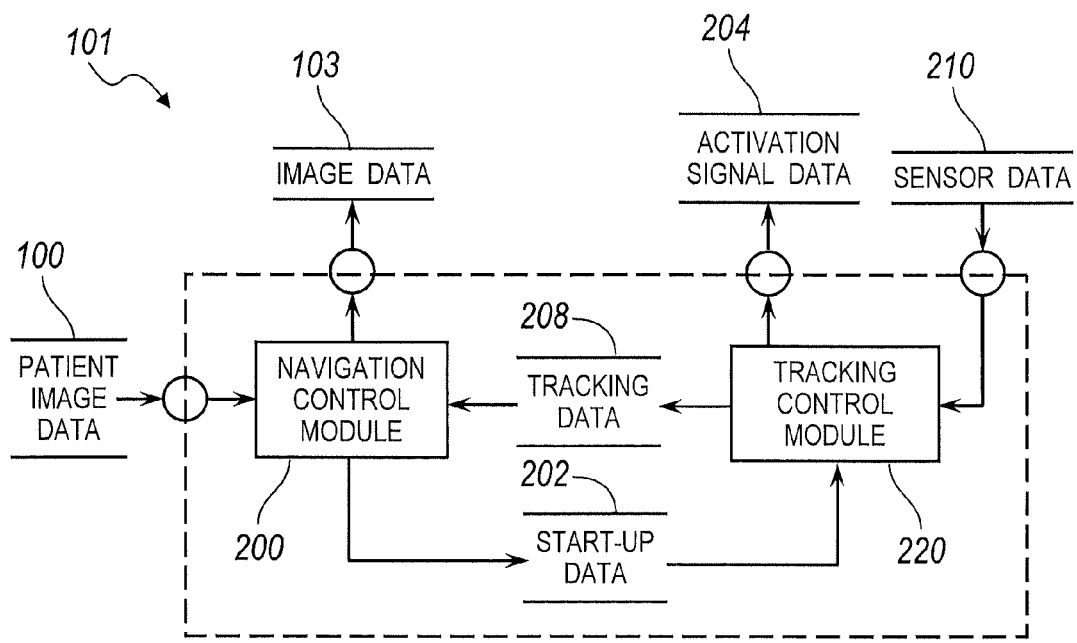
Figure 13:
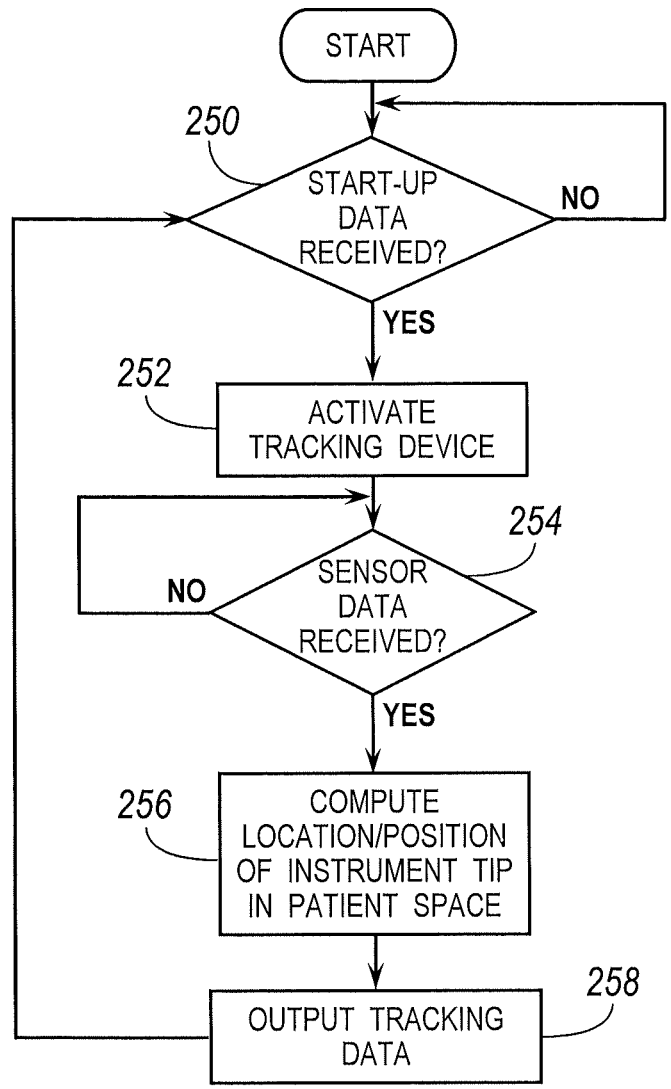

FIG. 5 a cross-sectional view of the navigated drill guide of FIG. 3 taken along line 5-5 of FIG. 3;

FIG. 6 is a perspective view of a navigated drill guide for use with the navigation system of FIG. 1;

FIG. 7 is an exploded view of the navigated drill guide of FIG. 6;

FIG. 8A is a cross-sectional schematic view of the navigated drill guide of FIG. 6, taken along line 8-8 of FIG. 6, illustrating a drill bit in a first position;

FIG. 8B is a detailed cross-sectional schematic view of a portion of the navigated drill guide of FIG. 8A;

FIG. 9 is a cross-sectional schematic view of the navigated drill guide of FIG. 6, taken along line 8-8 of FIG. 6, illustrating the drill bit in a second position;

FIG. 10 is a cross-sectional schematic view of the navigated drill guide of FIG. 6, taken along line 8-8 of FIG. 6, illustrating an instrument for use with the navigated drill guide of FIG. 1;

FIG. 11 is a simplified block diagram illustrating a navigation system that includes the navigated surgical instrument;

FIG. 12 is a dataflow diagram illustrating a control system performed by a control module; and FIG. 13 is a flowchart illustrating a control method performed by the control module.

DETAILED DESCRIPTION

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing a system and method for a navigated guide for use with a surgical procedure. It should be noted, however, that the present teachings could be applicable to any appropriate procedure in which it is desirable to determine a position and trajectory of an object that is hidden from view, such as a deep brain stimulator (DBS) probe. Further, as used herein, the term module refers to an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality. Therefore, it will be understood that the following discussions are not intended to limit the scope of the appended claims.

FIG. 1 is a diagram illustrating an overview of a navigation system 10 that can be used for various procedures. The navigation system 10 can be used to track the location of an implant, such as a spinal implant or orthopedic implant, relative to a patient 12. Also the navigation system 10 can track the position and orientation of various instruments. It should further be noted that the navigation system 10 may be used to navigate any type of instrument, implant, or delivery system, including: guide wires, arthroscopic systems, orthopedic implants, spinal implants, deep-brain stimulator (DBS) probes, etc. Moreover, these instruments may be used to navigate or map any region of the body. The navigation system 10 and the various instruments may be used in any appropriate procedure, such as one that is generally minimally invasive, arthroscopic, percutaneous, stereotactic, or an open procedure.

The navigation system 10 may include an imaging device 14 that is used to acquire pre-, intra-, or post-operative or real-time image data of a patient 12. Alternatively, various imageless systems can be used or images from atlas models can be used to produce patient images, such as those disclosed in U.S. Patent Pub. No. 2005-0085714, filed Oct. 16, 2003, entitled "METHOD AND APPARATUS FOR SURGICAL NAVIGATION OF A MULTIPLE PIECE CONSTRUCT FOR IMPLANTATION," incorporated herein by reference. The imaging device 14 can be, for example, a fluoroscopic x-ray imaging device that may be configured as an O-arm™ or a C-arm 16 having an x-ray source 18, an x-ray receiving section 20, an optional calibration and tracking target 22 and optional radiation sensors 24. It will be understood, however, that patient image data can also be acquired using other imaging devices, such as those discussed above and herein.

An imaging device controller 28, that can control the C-arm 16, can capture the x-ray images received at the x-ray receiving section 20 and store the images for later use. The controller 28 may also be separate from the C-arm 16 and/or control the rotation of the C-arm 16. For example, the C-arm 16 can move in the direction of arrow A or rotate about a longitudinal axis 12a of the patient 12, allowing anterior or lateral views of the patient 12 to be imaged. Each of these movements involves rotation about a mechanical axis 32 of the C-arm 16. The movements of the imaging device 14, such as the C-arm 16 can be tracked with a tracking device 33.

In the example of FIG. 1, the longitudinal axis 12a of the patient 12 is substantially in line with the mechanical axis 32 of the C-arm 16. This can enable the C-arm 16 to be rotated relative to the patient 12, allowing images of the patient 12 to be taken from multiple directions or about multiple planes. An example of a fluoroscopic C-arm X-ray device that may be used as the optional imaging device 14 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc. An exemplary O-arm™ imaging device is available from Medtronic Navigation Littleton of Littleton, Mass.

In operation, the imaging device 14 generates x-rays from the x-ray source 18 that propagate through the patient 12 and calibration and/or tracking target 22, into the x-ray receiving section 20. This allows direct visualization of the patient 12 and radio-opaque instruments in the cone of X-rays. It will be understood that the tracking target 22 need not include a calibration portion. The x-ray receiving section 20 generates image data representing the intensities of the received x-rays. Typically, the x-ray receiving section 20 includes an image intensifier that first converts the x-rays to visible light and a charge coupled device (CCD) video camera that converts the visible light into digital image data. X-ray receiving section 20 can also be a digital device that converts x-rays directly to digital image data for forming images, thus potentially avoiding distortion introduced by first converting to visible light. With this type of digital C-arm, which is generally a flat panel device, the optional calibration and/or tracking target 22 and the calibration process discussed below may be eliminated.

Also, the calibration process may be eliminated or not used at all for various procedures. Alternatively, the imaging device 14 may only take a single image with the calibration and tracking target 22 in place. Thereafter, the calibration and tracking target 22 may be removed from the line-of-sight of the imaging device 14.

Two dimensional fluoroscopic images that may be taken by the imaging device 14 are captured and stored in the controller 28. Multiple two-dimensional images taken by the imaging device 14 may also be captured and assembled to provide a larger view or image of a whole region of a patient, as opposed to being directed to only a portion of a region of the patient 12. For example, multiple image data of a patient's leg may be appended together to provide a full view or complete set of image data of the leg that can be later used to follow contrast agent, such as Bolus tracking.

Patient image data 100 can be forwarded from the controller 28 to a navigation computer and/or processor or workstation 34. It will also be understood that the image data is not necessarily first retained in the controller 28, but may also be directly transmitted to the workstation 34. The workstation 34 can include a display 36, a user input device 38 and a control module 101. The workstation 34 can also include or be connected to an image processor, navigation processor, and memory to hold instruction and data. The workstation 34 can provide facilities for displaying the patient image data 100 as an image on the display 36, saving, digitally manipulating, or printing a hard copy image of the received patient image data 100.

The user input device 38 can comprise any device, such as an user input device 38, that can enable a user to interface with the workstation 34, such as a touchpad, touch pen, touch screen, keyboard, mouse, wireless mouse, or a combination thereof. The user input device 38 allows a physician or user 39 to provide inputs to control the imaging device 14, via the C-arm controller 28, or adjust the display settings of the display 36.

The control module 101 can determine the location of the tracking device 58 with respect to the patient space, and can output image data 102 to the display 36. The image data 102 can comprise an icon 103 that provides an indication of the location of a tracking device with respect to the patient space, illustrated on the patient image data 100, as will be discussed herein. It should be noted that the patient image data 100 can comprise at least one of data from the navigation system 10, image data acquired by the imaging device 14, patient information entered by the user through the user input device 38, pre-operative images, or combinations thereof.

When the x-ray source 18 generates the x-rays that propagate to the x-ray receiving section 20, the radiation sensors 24 can sense the presence of radiation, which is forwarded to the controller 28, to identify whether or not the imaging device 14 is actively imaging. This information is also transmitted to a coil array controller 48, further discussed herein.

While the imaging device 14 is shown in FIG. 1, any other alternative 2D, 3D or 4D imaging modality may also be used. For example, any 2D, 3D or 4D imaging device, such as an O-arm™ imaging device, isocentric fluoroscopy, bi-plane fluoroscopy, ultrasound, computed tomography (CT), multi-slice computed tomography (MSCT), magnetic resonance imaging (MRI), high frequency ultrasound (HFU), positron emission tomography (PET), optical coherence tomography (OCT), intra-vascular ultrasound (IVUS), ultrasound, intra-operative CT or MRI may also be used to acquire 2D, 3D or 4D pre- or post-operative and/or real-time images or patient image data 100 of the patient 12. For example, an intra-operative MRI system, such as the PoleStar® MRI system sold by Medtronic, Inc. The images of the patient 12 may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sites within the patient 12. It should further be noted that the imaging device 14, as shown in FIG. 1, provides a virtual bi-plane image using a single-head C-arm fluoroscope as the imaging device 14 by simply rotating the C-arm 16 about at least two planes, which could be orthogonal planes, to generate two-dimensional images that can be converted to three-dimensional volumetric images. By acquiring images in more than one plane, the icon 103 representing the location of an impacter, stylet, reamer driver, taps, drill, deep-brain stimulator (DBS) probes, or other instrument, introduced and advanced in the patient 12, may be superimposed in more than one view and included in the image data 102 displayed on the display 36.

With continuing reference to FIG. 1, the navigation system 10 can further include an electromagnetic navigation or tracking system 44 that includes a localizer, such as a coil array 46 and/or second coil array 47, the coil array controller 48, a navigation probe interface 50, a device or instrument 52 (e.g. catheter, needle, DBS probe, etc., as discussed herein), a dynamic reference frame (DRF) 54 and one or more tracking devices 58. Other tracking systems can include an optical tracking system 44b, for example the StealthStation® Treon® and the StealthStation® Tria® both sold by Medtronic Navigation, Inc. Further, other tracking systems include acoustic, radiation, radar, infrared, etc., or a hybrid system, such as a system that includes components of both an electromagnetic and optical tracking system, etc. The instrument 52 and the DRF 54 can each include the tracking device(s) 58.

The tracking device 58 or any appropriate tracking device as discussed herein, can include both a sensor, a transmitter, or combinations thereof and can be indicated by the reference numeral 58. Further, the tracking devices 58 can be wired or wireless to provide a signal or emitter or receive a signal from a system. Nevertheless, a tracking device 58a can include an electromagnetic coil to sense a field produced by the localizing coil array 46 or 47, while a tracking device 58b can include reflectors that can reflect a signal to be received by the optical localizer or tracking system 44b. Nevertheless, one will understand that the tracking device(s) 58 can receive a signal, transmit a signal, or combinations thereof to provide information to the navigation system 10 to determine a location of the tracking device 58. In addition, it will be understood that the tracking device 33 of the C-arm 16 could comprise a suitable tracking device 58. The navigation system 10 can then determine a position of the instrument 52 based on the location of the tracking device 58 to allow for navigation relative to the patient 12 and the patient space.

With regard to the optical localizer or tracking system 44b, the optical tracking system 44b can transmit and receive an optical signal, or combinations thereof. An optical tracking device 58b can be interconnected with the instrument 52, or other devices such as the DRF 54. As generally known, the optical tracking device 58b can reflect, transmit or receive an optical signal to/from the optical localizer or tracking system 44b that can be used in the navigation system 10 to navigate or track various elements. Therefore, one skilled in the art will understand, that the tracking devices 58 can be any appropriate tracking device to work with any one or multiple tracking systems.

An electromagnetic tracking system 44 can include the coil arrays 46, 47 but the coil arrays 46, 47 may also be supplemented or replaced with a mobile localizer (not shown). The mobile localizer may be one such as that described in U.S. patent application Ser. No. 10/941,782, filed Sep. 15, 2004, and entitled "METHOD AND APPARATUS FOR SURGICAL NAVIGATION", herein incorporated by reference. As is understood, the coil array 46, 47 can transmit signals that are received by the tracking device(s) 58. The tracking device(s) 58 can then transmit or receive signals based upon the transmitted or received signals from or to the coil arrays 46, 47.

Further included in the navigation system 10 may be an isolator circuit or assembly (not specifically shown). The isolator circuit or assembly may be included in a transmission line to interrupt a line carrying a signal or a voltage to the navigation probe interface 50. Alternatively, the isolator circuit included in the isolator box may be included in the navigation probe interface 50, the instrument 52, the DRF 54, the transmission lines coupling the instruments 52, or any other appropriate location. The isolator assembly is operable to isolate any of the instruments or patient coincidence instruments or portions that are in contact with the patient 12 should an undesirable electrical surge or voltage take place.

In addition, the navigation system 10 can further include a gating device or an ECG or electrocardiogram (not shown), which is attached to the patient 12, via skin electrodes, and in communication with the coil array controller 48. Respiration and cardiac motion can cause movement of cardiac structures relative to the instrument 52, even when the instrument 52 has not been moved. Therefore, images can be acquired from the imaging device 14 based on a time-gated basis triggered by a physiological signal. For example, the ECG or EGM signal may be acquired from the skin electrodes or from a sensing electrode included on the instrument 52 or from a separate reference probe (not shown). A characteristic of this signal, such as an R-wave peak or P-wave peak associated with ventricular or atrial depolarization, respectively, may be used as a triggering event for the coil array controller 48 to drive the coils in the coil arrays 46, 47. This triggering event may also be used to gate or trigger image acquisition during the imaging phase with the imaging device 14. By time-gating the image data 102 and/or the navigation data, the icon 103 of the location of the instrument 52 in image space relative to the patient space at the same point in the cardiac cycle may be displayed on the display 36. Further detail regarding the time-gating of the image data and/or navigation data can be found in U.S. Pub. Application No. 2004-0097806, entitled "Navigation System for Cardiac Therapies," filed Nov. 19, 2002, which is hereby incorporated by reference.

It should further be noted that the entire electromagnetic tracking system 44 or parts of the electromagnetic tracking system 44 may be incorporated into the imaging device 14, including the radiation sensors 24, the workstation 34 and the control module 101. Incorporating the electromagnetic tracking system 44 can provide an integrated imaging and tracking system. Any combination of these components can also be incorporated into the imaging device 14, which again can include a fluoroscopic C-arm imaging device or any other appropriate imaging device.

The coil arrays 46, 47 are shown attached to the operating table 49. It should be noted, however, that the coil arrays 46, 47 can also be positioned at any other location as well and can also be positioned in the items being navigated. The coil arrays 46, 47 include a plurality of coils that are each operable to generate distinct electromagnetic fields into the navigation region of the patient 12, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil arrays 46, 47 can be controlled or driven by the coil array controller 48. The coil array controller 48 can drive each coil in the coil arrays 46, 47 in a time division multiplex or a frequency division multiplex manner. In this regard, each coil can be driven separately at a distinct time or all of the coils can be driven simultaneously with each being driven by a different frequency. Upon driving the coils in the coil arrays 46, 47 with the coil array controller 48, electromagnetic fields are generated within the patient 12 in the area where the medical procedure is being performed, which is again sometimes referred to as patient space. The electromagnetic fields generated in the patient space induce currents in a tracking device(s) 58 positioned on or in the instrument 52. These induced signals from the instrument 52 are delivered to the navigation probe interface 50 and can be subsequently forwarded to the coil array controller 48.

The navigation probe interface 50 may provide all the necessary electrical isolation for the navigation system 10. The navigation probe interface 50 can also include amplifiers, filters and buffers to directly interface with the tracking device 58 in the instrument 52. Alternatively, the tracking device 58, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

Various portions of the navigation system 10, such as the instrument 52, the DRF 54 and others as will be described in detail below, are equipped with at least one, and generally multiple, tracking devices 58, that may also be referred to as localization sensors. The tracking device 58 can be a handle or inserter that interconnects with an attachment and may assist in placing an implant. The instrument 52 can include a graspable or manipulable portion at a proximal end and the tracking device 58 may be fixed near the manipulable portion of the instrument 52. The instrument 52 may be any appropriate instrument, such as an instrument for preparing a portion of the patient 12 or an instrument for positioning an implant.

In an alternate embodiment, the electromagnetic sources or generators may be located within the instrument 52, DRF 54, and one or more receiver coils may be provided externally to the patient 12 forming a receiver coil array similar to the coil arrays 46, 47. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The DRF 54 of the tracking system 44 can also be coupled to the navigation probe interface 50 to forward the information to the coil array controller 48. The DRF 54, according to various embodiments, can include a small magnetic field detector. The DRF 54 may be fixed to the patient 12 adjacent to the region being navigated so that any movement of the patient 12 is detected as relative motion between the coil arrays 46, 47 and the DRF 54. This relative motion can be forwarded to the coil array controller 48, which can update the registration correlation and maintain accurate navigation, as further discussed herein. The DRF 54 may include any appropriate tracking device(s) 58 used by the navigation system 10. Therefore, the DRF 54 can include an optical tracking device, as indicated by reference number 58b, or acoustic, etc. If the DRF 54 is used with an electromagnetic tracking device 58a it can be configured as a pair of orthogonally oriented coils, each having the same center or may be configured in any other non-coaxial or co-axial coil configurations (not specifically shown).

Briefly, the navigation system 10 operates as follows. The navigation system 10 creates a translation map between all points in the radiological image generated from the imaging device 14 and the corresponding points in the patient's anatomy in patient space. After this map is established, whenever a tracked instrument, such as the instrument 52 is used, the workstation 34 in combination with the coil array controller 48 and the controller 28 uses the translation map to identify the corresponding point on the pre-acquired image or atlas model, which is displayed on display 36. This identification is known as navigation or localization. The icon 103 representing the localized point or instruments 52 can be shown as image data 102 on the display 36, as will be discussed herein.

To enable navigation, the navigation system 10 must be able to detect both the position of the patient's anatomy and the position of the instrument 52 or attachment member (e.g., tracking device 58) attached to the instrument 52. Knowing the location of these two items allows the navigation system 10 to compute and display the position of the instrument 52 in relation to the patient 12 on the display 36. The tracking system 44 can be employed to track the instrument 52 and the anatomy simultaneously.

The tracking system 44, if using an electromagnetic tracking assembly, essentially works by positioning the coil arrays 46, 47 adjacent to the patient space to generate a low-energy magnetic field generally referred to as a navigation field. Because every point in the navigation field or patient space is associated with a unique field strength, the tracking system 44 can determine the position of the instrument 52 by measuring the field strength at the tracking device 58 location. The DRF 54 is fixed to the patient 12 to identify the location of the patient 12 in the navigation field. The tracking system 44 continuously recomputes the relative position of the DRF 54 and the instrument 52 during localization and relates this spatial information to patient registration data to enable image guidance of the instrument 52 within and/or relative to the patient 12.

Patient registration is the process of determining how to correlate the position of the instrument 52 relative to the patient 12 to the position on the diagnostic or pre-acquired images. To register the patient 12, a physician or user 39 may use point registration by selecting and storing particular points from the pre-acquired images and then touching the corresponding points on the patient's anatomy with a pointer probe (not shown). The navigation system 10 analyzes the relationship between the two sets of points that are selected and computes a match, which correlates every point in the image data 102 with its corresponding point on the patient's anatomy or the patient space, as discussed herein. The points that are selected to perform registration are the fiducial markers 60, such as anatomical landmarks. Again, the landmarks or fiducial markers 60 are identifiable on the images and identifiable and accessible on the patient 12. The fiducial markers 60 can be artificial markers that are positioned on the patient 12 or anatomical landmarks that can be easily identified in the image data 102. The artificial landmarks, such as the fiducial markers 60, can also form part of the DRF 54, such as those disclosed in U.S. Pat. No. 6,381,485, entitled "Registration of Human Anatomy Integrated for Electromagnetic Localization," issued Apr. 30, 2002, herein incorporated by reference.

The navigation system 10 may also perform registration using anatomic surface information or path information as is known in the art. The navigation system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 60/465,615, entitled "Method and Apparatus for Performing 2D to 3D Registration" filed on Apr. 25, 2003, hereby incorporated by reference.

Also as discussed herein, a substantially fiducial-less registration system can be provided, particularly if the imaging device 14 and the tracking system 44 are substantially integrated. Therefore, the tracking system 44 would generally know the position of the imaging device 14 relative to the patient 12 and fiducial markers 60 may not be required for registration. Nevertheless, it will be understood that any appropriate type of registration system can be provided for the navigation system 10.

In order to maintain registration accuracy, the navigation system 10 continuously tracks the position of the patient 12 during registration and navigation. This is because the patient 12, DRF 54, and coil arrays 46, 47 may all move during the procedure, even when this movement is not desired. Alternatively the patient 12 may be held immobile once the registration has occurred, such as with a head frame (not shown). Therefore, if the navigation system 10 did not track the position of the patient 12 or area of the anatomy, any patient movement after image acquisition would result in inaccurate navigation within that image. The DRF 54 allows the tracking system 44 to register and track the anatomy. Because the DRF 54 is rigidly fixed to the patient 12, any movement of the anatomy or the coil arrays 46, 47 is detected as the relative motion between the coil arrays 46, 47 and the DRF 54. This relative motion is communicated to the coil array controller 48, via the navigation probe interface 50, which updates the registration correlation to thereby maintain accurate navigation.

The navigation system 10 can be used according to any appropriate method or system. For example, pre-acquired images, atlas or 3D models may be registered relative to the patient 12 and the patient space. Generally, the navigation system 10 allows the images on the display 36 to be registered and to accurately display the real time location of the various instruments, such as the instrument 52, and other appropriate items, such as DRF 54. In addition, the DRF 54 may be used to ensure that any planned or unplanned movement of the patient 12 or the coil arrays 46, 47 can be determined and used to correct the image data 102 on the display 36.

Figure 2A:
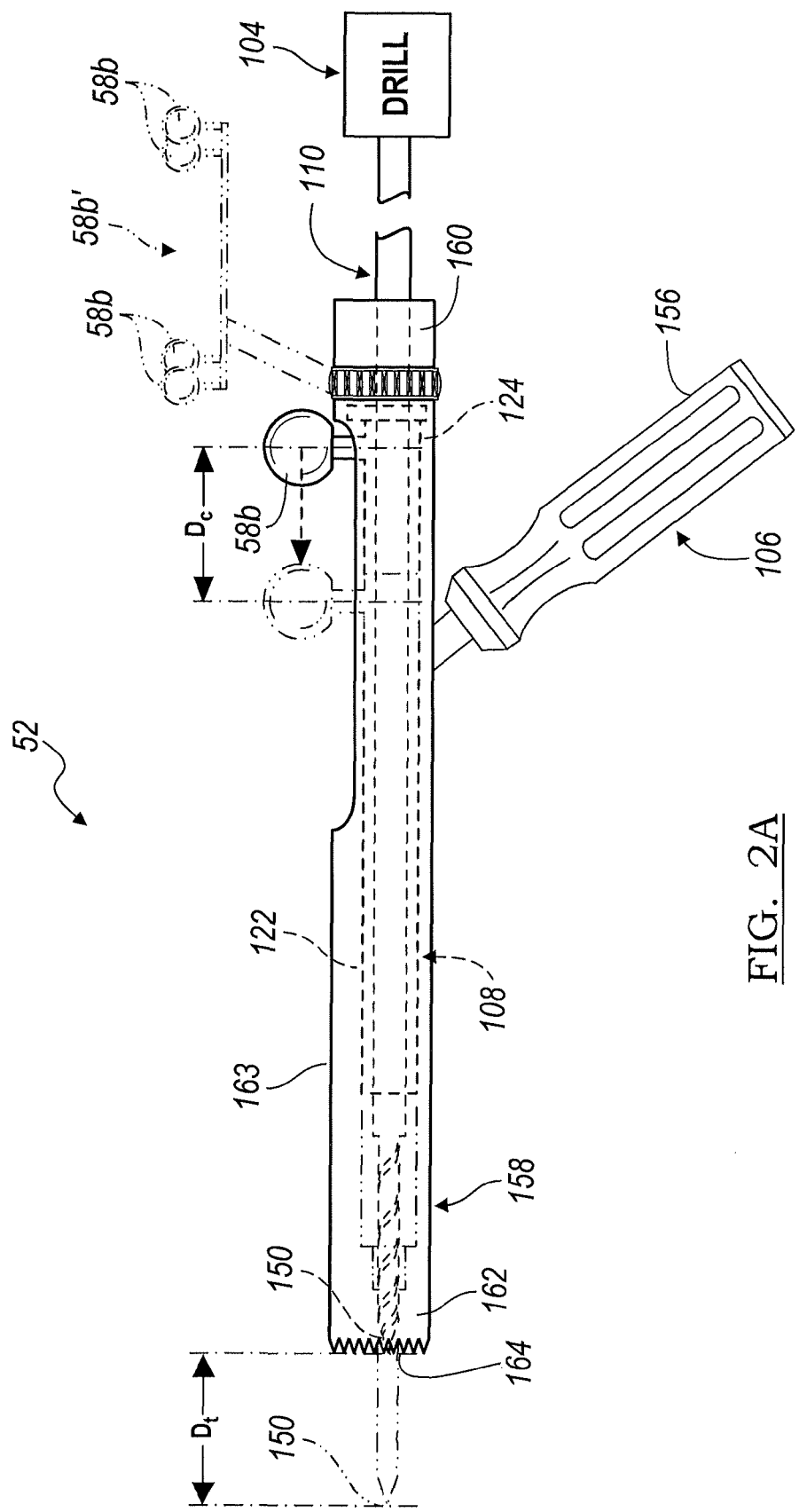
FIG. 2A is a schematic illustration of a navigated drill guide for use with the navigation system of FIG. 1.

Referring now to FIG. 2A, instruments 52 are shown for use with the optical tracking system 44b. In this example, the instruments 52 can include a drill 104 and a drill guide 106.

The drill 104 can include a sleeve 108 and a drill bit 110. The drill bit 110 can comprise a conventional drill bit that can engage and remove portions of an anatomy of the patient 12, and thus, will not be discussed in great detail herein.

The sleeve 108 can include an optical tracking device 58b, which can be coupled to a body 122 of the sleeve 108. As will be discussed in greater detail below, the body 122 of the sleeve 108 can be configured to receive the drill bit 110 therethrough. With regard to the tracking device 58b, the tracking device 58b can be coupled to a proximal end 124 of the body 122 of the sleeve 108. The tracking device 58b can be responsive to the optical tracking system 44b, and thus, can include at least one optical reflector or at least one optical transmitter, or combinations thereof, depending upon the optical tracking system 44b employed with the navigation system 10. Further, it should be noted, that although one tracking device 58b is illustrated, any number of tracking devices 58 could be employed, such as an array or a tracking device 58b' illustrated in phantom on the drill guide 106, and further, it will be understood that the tracking device 58b' can be arranged with any appropriate number of tracking devices 58b, such as three, and further the tracking device 58b' could be arranged in any appropriate pattern or configuration.

With continued reference to FIGS. 1 and 2A, the drill guide 106 can comprise any suitable guide that enables the user 39 to direct the motion of the drill bit 110, and can include a handle 156 and a cannula 158. As the handle 156 can comprise any suitable graspable or manipulable portion, the handle 156 of the drill guide 106 will not be discussed in greater detail below.

The cannula 158 can include a proximal end 160, a distal end 162, and a tube 163 that can couple the proximal end 160 to the distal end 162. The proximal end 160, the distal end 162 and the tube 163 can define an opening or throughbore 164. The cannula 158 can also include the optical tracking device 58b', if desired. The tracking device 58b' can be optional, and if employed, can be coupled to the proximal end 160 of the cannula 158. The tracking device 58b' can include one or more optical tracking devices 58b arranged in a suitable pattern to enable the navigation system 10 to determine the location of the drill guide 106 in patient space. The tracking device 58b' can be responsive to the optical tracking system 44b, and thus, can include one or more optical reflectors or one or more optical transmitters, or combinations thereof, depending upon the optical tracking system 44b employed with the navigation system 10. Further, it should be noted that although four tracking devices 58b are illustrated, any number of tracking devices 58b could be employed. In addition, in the case of a hybrid tracking system 44, an electromagnetic tracking device 58 could be employed for use with the drill guide 106 or sleeve 108 or vice versa.

In order to assemble the instruments 52, the sleeve 108 can be inserted into the cannula 158, and then the drill bit 110 can be inserted into the sleeve 108. Then, the user 39 (FIG. 1) can use the drill bit 110 to engage the anatomy. In order to engage the anatomy of the patient 12, the user 39 can move the drill 104, and thus, the sleeve 108 and the drill bit 110, within the drill guide 106 such that as the drill bit 110 advances into the anatomy, the sleeve 108 moves relative to the proximal end 160 of the cannula 158. As the sleeve 108 moves, the tracking system 44b can track the location of the tracking device 58b, and thus, can track the location of the distal end of the instrument 52. In this regard, as the location of the tracking device 58b relative to the sleeve 108 is known, the tracking system 44 can track the distal end of either the drill guide 106 (distal end 162) or the drill bit 110 (tip 150). The tracking system 44b can track the distal end 162 of the cannula 158 when the tracking device 58b remains in its first or initial position, as illustrated in FIG. 2A. As the sleeve 108 can move into a second position as the drill bit 110 advances, the movement of the sleeve 108 can cause the tracking device 58b to move a distance $D_c$ that can correspond to a distance $D_t$ that the tip 150 extends beyond the cannula 158 (as shown in phantom). Thus, based on the displacement of the tracking device 58b relative to the cannula 158, the navigation system 10 can determine the distal end 162 of the cannula 158 or the tip 150 of the drill bit 110 based on the location of the tracking device 58b.

In this regard, the single tracking device 58b can provide one degree of freedom information for the navigation system 10, while the tracking device 58b' can provide at least three to six degrees of freedom information for the navigation system 10. Therefore, if the single tracking device 58b is employed with the sleeve 108 and the tracking device 58b' is employed with the cannula 158, then the navigation system 10 can determine the direction or orientation of the cannula 158 by tracking the tracking device 58b' and can determine the depth or distance traveled by the sleeve 108 relative to the cannula 158 by tracking the tracking device 58b. It will be understood, however, that the sleeve 108 could include at least three tracking devices 58b, which would provide the navigation system 10 with at least three degrees of freedom information for the sleeve 108. If the sleeve 108 has at least three tracking devices 58b, then based on the tracking of the tracking devices 58b of the sleeve 108, the navigation system 10 could determine the direction or orientation of the sleeve 108 with or without the tracking device 58b' on the cannula 158. It should be understood, however, that any appropriate configuration could be employed to track the movement of the distal end 150 of the drill bit 110 relative to the anatomy.

Figure 2B:
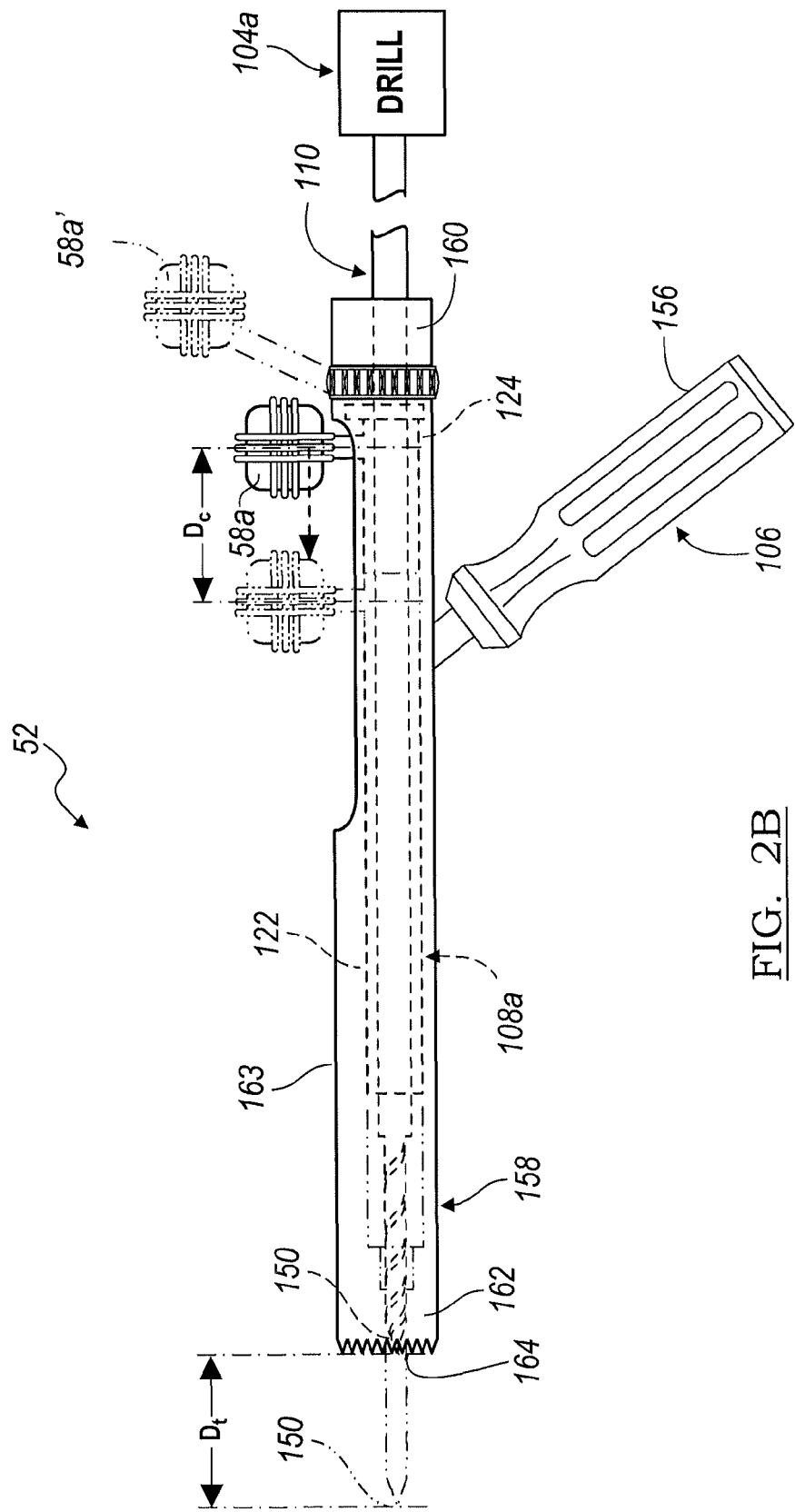
FIG. 2B is a schematic illustration of a navigated drill guide for use with the navigation system of FIG. 1.

Referring now to FIG. 2B, instruments 52 are shown for use with the electromagnetic tracking system 44. As the instruments 52 can comprise the same or similar components as the instruments 52 discussed with regard to FIG. 2A, the same reference numerals will be used herein. In this example, the instruments 52 can include a drill 104a and the drill guide 106. The drill 104a can include a sleeve 108a and the drill bit 110. As the drill guide 106 and drill bit 110 illustrated in FIG. 2B can be substantially similar to the drill guide 106 and drill bit 110 illustrated and described with regard to FIG. 2A, the drill guide 106 and drill bit 110 will not be discussed in great detail herein with regard to FIG. 2B. Briefly, however, the cannula 158 of the drill guide 106 can include an electromagnetic tracking device 58a', if desired. The tracking device 58a' can be optional, and if employed, can be coupled to the proximal end 160 of the cannula 158. The tracking device 58a' will be discussed in greater detail herein with regard to the sleeve 108a.

The sleeve 108a can include an electromagnetic tracking device 58a, which can be coupled to the body 122 of the sleeve 108a. With regard to the tracking device 58a, the tracking device 58a can be coupled to the proximal end 124 of the body 122 of the sleeve 108a. The tracking device 58a, and the tracking device 58a', can be responsive to the electromagnetic tracking system 44, and thus, can include at least one electromagnetic receiver or at least one electromagnetic transmitter, or combinations thereof, depending upon the electromagnetic tracking system 44 employed with the navigation system 10. For example, the tracking device 58a and the tracking device 58a' can comprise any suitable electromagnetic transmitters or electromagnetic receivers, and can have any suitable coil configuration, such as a dual coil, tri-axial coil, dual orthogonal coils, dual collinear coils, a delta coil pair or combinations thereof. It should be noted that although the tracking device 58a and tracking device 58a' are illustrated in the field of view or exposed, it is not necessary for the tracking device 58a and the tracking device 58a' to be within the field of view, and the tracking device 58a and the tracking device 58a' can be easily embedded in the instruments 52 and out of the way of surgeon. In addition, in the case of a hybrid tracking system 44, an optical tracking device 58b could be employed for use with the drill guide 106 or sleeve 108a or vice versa.

In order to assemble the instruments 52, the sleeve 108a can be inserted into the cannula 158, and then the drill bit 110 can be inserted into the sleeve 108a. Then, the user 39 (FIG. 1) can use the drill bit 110 to engage the anatomy. As discussed, the user 39 can move the drill 104a, and thus, the sleeve 108a and the drill bit 110, within the drill guide 106 such that as the drill bit 110 advances into the anatomy, the sleeve 108a moves relative to the proximal end 160 of the cannula 158. As the sleeve 108a moves, the electromagnetic tracking system 44 can track the location of the tracking device 58a, and thus, can track the location of the distal end of the instrument 52. In this regard, as the location of the tracking device 58a relative to the sleeve 108a is known, the tracking system 44 can track the distal end of either the drill guide 106 (distal end 162) or the drill bit 110 (tip 150).

The tracking system 44 can track the distal end 162 of the cannula 158 when the tracking device 58a remains in its first or initial position, as illustrated in FIG. 2B. As the sleeve 108a can move into a second position as the drill bit 110 advances, the movement of the sleeve 108a can cause the tracking device 58a to move a distance $D_c$ that can correspond to a distance $D_t$ that the tip 150 extends beyond the cannula 158 (as shown in phantom). Thus, based on the displacement of the tracking device 58a relative to the cannula 158, the navigation system 10 can determine the distal end 162 of the cannula 158 or the tip 150 of the drill bit 110 based on the location of the tracking device 58a.

In this regard, the single tracking device 58a can provide at least three and up to six degrees of freedom information for the navigation system 10. Therefore, based on the tracking of the tracking device 58a of the sleeve 108a, the navigation system 10 could determine the direction or orientation of the sleeve 108a with or without the tracking device 58a' on the cannula 158. It should be understood, however, that any appropriate configuration could be employed to track the movement of the distal end 150 of the drill bit 110 relative to the anatomy.

With reference now to FIG. 3, exemplary instruments 52 for use with the electromagnetic tracking system 44 are shown. As the instruments 52 can comprise the same or similar components as the instruments 52 discussed with regard to FIGS. 2A and 2B, the same reference numerals will be used herein. In this example, a first instrument 52 is a drill 104b and a second instrument 52 is a drill guide 106b, however, as will be evident from the teachings herein, various other instruments 52 could employ a tracking device 58c as will be discussed herein, such as an instrument 52 in which it is desirable to measure a position and a trajectory of the instrument 52, for example, a DBS probe or a catheter. As the drill 104b can comprise a conventional drill for the anatomy, the drill 104b will not be discussed in great detail herein. Briefly, however, as illustrated in FIG. 3, the drill 104b can comprise a sleeve 108b and a drill bit 110b. The drill 104b can be activated by the user 39 to advance or retract the sleeve 108b and the drill bit 110b into the anatomy of the patient 12.

The sleeve 108b can include a connector 116, a spring 118, a bushing 120 and the tracking device 58c, each of which can be coupled to the body 122 of the sleeve 108b. With additional reference to FIG. 4, the connector 116 can be coupled to the proximal end 124 of the body 122 of the sleeve 108b. The connector 116 can be generally horseshoe-shaped, and can include a first portion 126 and a second portion 128. The first portion 126 can be cylindrical to couple the connector 116 to the sleeve 108b. The first portion 126 can be press-fit to the sleeve 108b, or could be bonded or mechanically fastened to the sleeve 108b. In addition, as illustrated, the connector 116 can have a clamshell design such that coupling of the respective second portions 128 can couple the first portion 126 to the body 122 of the sleeve 108b.

The second portion 128 can include a controller 130b. The controller 130b can receive the current induced in the tracking device or coil 58c that is coupled to the drill 104b when the instrument 52 is placed in the patient space or EM field. The controller 130b can receive the current from the tracking device 58c, and can transmit a signal indicative of the current of the tracking device 58c to the navigation probe interface 50. One or more cables 132 can be in communication with the tracking device 58c and the controller 130b to transmit the current from the tracking device 58c to the controller 130b. At least one cable 132a can be in communication with the controller 130b to receive the current from the tracking device 58c, and can transmit the current to the navigation probe interface 50. It will be understood, however, that although a wired connection is illustrated herein, any suitable technique could be used to transmit the current from the tracking device 58c to the controller 130b and the navigation probe interface 50, such as a wireless connection.

The spring 118 can be a helical spring, and can be coiled around the body 122 of the sleeve 108b, near the proximal end 124. The spring 118 can include a first end 136 and a second end 138. The first end 136 of the spring 118 can abut the connector 116, such that the connector 116 can retain the spring 118 on the body 122 of the sleeve 108b. The second end 138 can include a narrowly coiled section 138a that can retain the spring 118 on the body 122 of the sleeve 108b, but can enable the spring 118 to be compressed against the drill guide 106b.

The bushing 120 can be coupled to a distal end 140 of the body 112 of the sleeve 108b. The bushing 120 can facilitate the easy insertion of the sleeve 108b into the drill guide 106b. It should be noted, however, that the bushing 120 can be optional and need not be included in the sleeve 108b. The bushing 120 can form a tip 141 of the sleeve 108b. Spring 118 can assist in removing the sleeve 108 from the drill guide 106b as will be discussed.

The tracking device 58c can be coupled to the body 122 of the sleeve 108b. The tracking device 58c can comprise one or more electromagnetic sensors or coils 142. Generally, the electromagnetic coils 142 can comprise a tightly coiled conductive wire in which a current can be induced when the electromagnetic field is generated by the coil arrays 46, 47. The electromagnetic coils 142 can be in communication with the controller 130b of the connector 116 to transmit the induced current to the controller 130b. For example, the electromagnetic coils 142 could be connected to the controller 130 via a cable 132a as shown in FIG. 3. Alternatively, the electromagnetic coils 142 could be in wireless communication with the controller 130 (not shown). Given that each point in the patient space has a unique field strength, the current induced in the electromagnetic coils 142 can be representative of the physical location of the electromagnetic coils 142 in the patient space, if the electromagnetic coils 142 are receiver electromagnetic coils 142. Alternatively, if the electromagnetic coils 142 are transmitter electromagnetic coils 142, then the magnetic field generated or produced by the electromagnetic coils 142 can vary based on the physical location of the electromagnetic coils 142 in the patient space. The coil array controller 48 can then determine the physical location of the instrument 52 based on the known location of the tracking device 58c with respect to the instrument 52. The electromagnetic coils 142 can be positioned adjacent to the distal end 140 of the sleeve 108b to enable the tracking system 44 to track the distal end 140 of the drill guide 106b and the drill bit 110b when the tracking device 58c is positioned within the drill guide 106b, as will be discussed.

Generally, two electromagnetic coils 142 can be positioned adjacent to the distal end 140 of the instrument 52, in this case the sleeve 108b of the drill 104, to enable the continuous calibration of the instrument 52. In this regard, traditionally a calibration detent is used to determine a distance from the tracking device 58 to the distal end 162 of the instrument 52. In this example, the placement of at least two electromagnetic coils 142 near the distal end 162 of the instrument 52 can enable the tracking system 44 to continuously monitor the instrument 52 for changes in a distance D4 between the electromagnetic coils 142 that would indicate that the instrument 52 has been bent, twisted or deformed. In this regard, the tracking system 44 can compare the actual distance D4 between a first electromagnetic coil 142a and a second electromagnetic coil 142b based on the current induced by the coil arrays 46, 47 to a known or predicted distance D4 between the first electromagnetic coil 142a and the second electromagnetic coil 142b. Based on the comparison, the navigation system 10 can notify the user 39 of a change in the accuracy of the instrument 52, and can also compensate for the change in the shape of the instrument 52, if so desired.

The body 122 of the sleeve 108b can define a throughbore 146. The body 122 of the sleeve 108b can be composed of a non-ferrous material, such as plastic and/or titanium, for example. The throughbore 146 of the body 122 can enable the receipt of the drill bit 110 within the sleeve 108b. Generally, the throughbore 146 is sized such that the drill bit 110 can rotate freely within the sleeve 108b, and can extend beyond the distal end 140 of the sleeve 108b to contact an anatomy of the patient 12.

Figure 4:
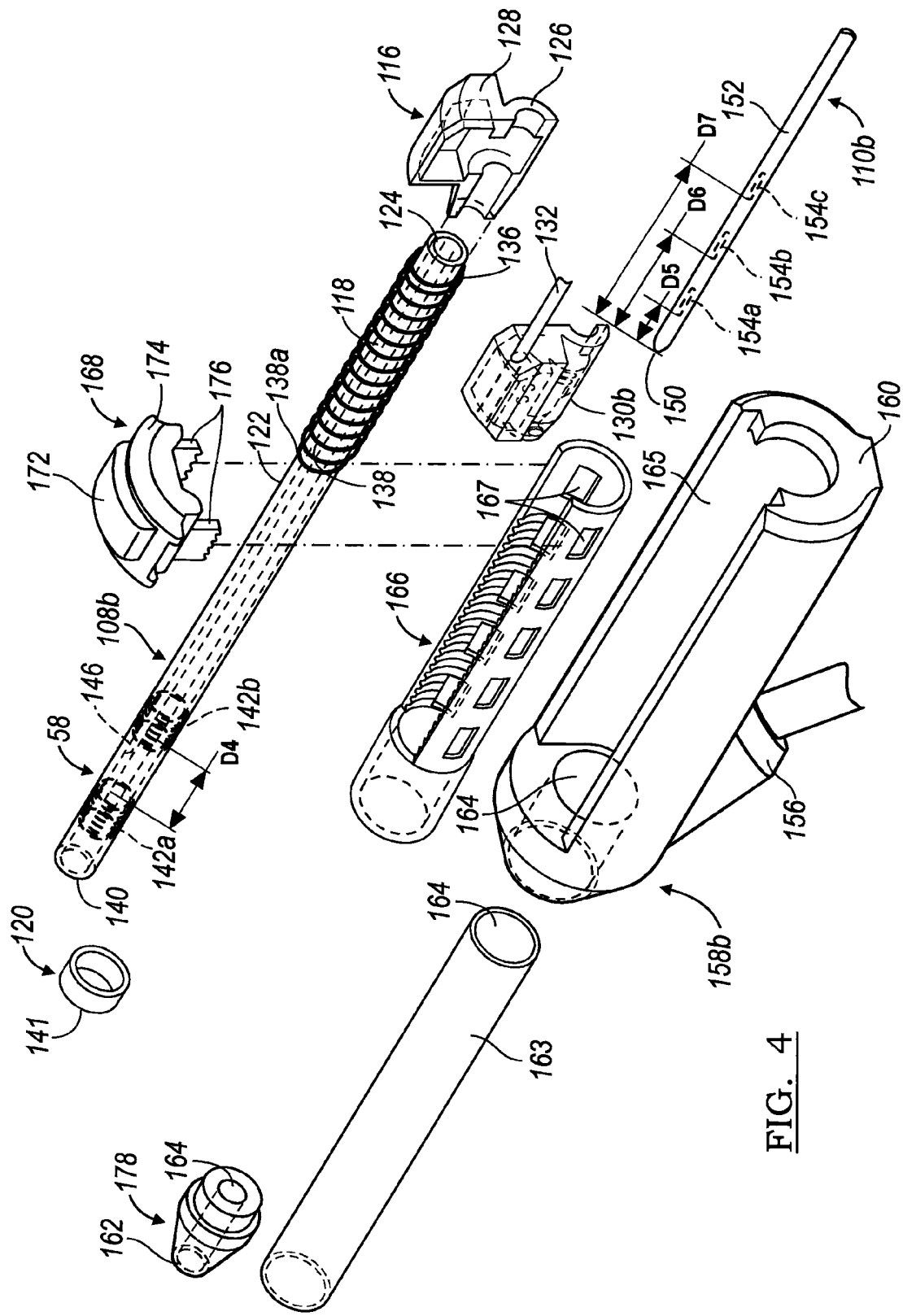
FIG. 4 is an exploded view of the navigated drill guide of FIG. 3.

With reference to FIG. 4, the drill bit 110b can include the tip 150 and a body 152. The tip 150 can generally be pointed such that the tip 150 can engage the anatomy of the patient 12 to remove a selected portion of the anatomy. The body 152 can include one or more segments 154 composed of a distinct or unique non-ferrous material with respect to the remainder of the body 152 of the drill bit 110b to enable the navigation system 10 to identify the trajectory and/or position of the drill bit 110.

For example, as shown in FIG. 4, the body 152 can include a first segment 154a, a second segment 154b, and a third segment 154c. In this example, the first segment 154a can be disposed a distance D5 from the tip 150 of the drill bit 110b, while the second segment 154b can be spaced apart from the first segment 154a by a known distance D6. The third segment 154c is spaced a known distance D7 apart from the second segment 154b. It should be noted that the distances D5, D6, D7 can be equal to each other, or each of the distances D5, D6, D7 can have a distinct value that can be greater than, less than or equal to the other distances D5, D6, D7, as desired. For example, the distance D5 can be less than distance D6 and D7, and distance D6 can be less than distance D7 to enable fine movements of the drill bit 110b to be tracked by the tracking system 44. Thus, the distances D5, D6, D7 between the segments 154 enable the movement of the drill bit 110b to be accurately tracked by the tracking system 44, as will be discussed herein. In addition, the number of segments 154 formed on the body 152 can enable fine or coarse tracking of the drill bit 110b. For example, if fine tracking of the drill bit 110b is desired, a large number of segments 154 can be formed on the body 152 (not shown).

In this example, each of the segments 154 can be composed of a first non-ferrous metal or metal alloy, while the remainder of the drill bit 110b can be composed of a second non-ferrous metal or metal alloy. Thus, a different, distinct non-ferrous material can separate each of the segments 154. As each of the segments 154 can be adjacent to a unique non-ferrous material, the position and trajectory of the drill bit 110b can be determined or computed by the coil array controller 48. In this regard, the use of the unique segments 154 of material in the body 152 of the drill bit 110b can result in a change in the inductance of the electromagnetic coils 142 due to the varying permeability of the segments 154 of the drill bit 110b. As the electromagnetic coils 142 can be wound around the body 122 of the sleeve 108b, as best shown in FIG. 5, the movement of the drill bit 110b within the sleeve 108b can change the current induced in the electromagnetic coils 142 due to the differing core materials that comprise the segments 154, which pass through the electromagnetic coils 142 during the movement of the drill bit 110b, in the exemplary case of receiver electromagnetic coils 142. In another example, if the electromagnetic coils 142 comprise transmitter electromagnetic coils 142, then the magnetic field generated or produced by the electromagnetic coils 142 can vary with the movement of the drill bit 110b due to the change in the permeability of the material comprising the segments 154.

In this regard, the amount of current generated by the electromagnetic coils 142 can increase or decrease based on whether a segment 154 or the body 152 of the drill bit 110b is positioned within the electromagnetic coil 142. Thus, as a length of the drill bit 110b is known, and the length, location and material of the segments 154 of the drill bit 110b are known, given the amount of current induced in the electromagnetic coils 142 during the movement of the drill bit 110b, the coil array controller 48 can compute the position and trajectory of the tip 150 of the drill bit 110b in the patient space, as will be discussed further herein.

With continued reference to FIG. 4, as the drill guide 106b can comprise any suitable guide that enables the user 39 to direct the motion of the drill bit 110b within the anatomy, the drill guide 106b, will not be described in great detail herein. Briefly, however, the drill guide 106b can comprise the handle 156 and a cannula 158b. The handle 156 can comprise any suitable graspable or manipulable portion that is configured to enable the manipulation of the drill guide 106b by the user 39. The cannula 158b can include a proximal end 160, a distal end 162 coupled to the proximal end 160 via a tube 163, with the proximal end 160, distal end 162 and tube 163 defining an opening or throughbore 164 therethrough. The cannula 158b can be coupled to the handle 156 at any desired angle that facilitates the manipulation of the drill 104, and generally, can be coupled to the handle 156 near the proximal end 160. The proximal end 160 of the cannula 158b can define a slot 165 that can receive an insert 166 and a stop 168.

The insert 166 can be configured to receive the sleeve 108b. The insert 166 can be threadably coupled to the proximal end 160 of the cannula 158b, or the insert 166 can be press-fit into the cannula 158b. The insert 166 can enable the sleeve 108b to be inserted into and properly aligned in the cannula 158b. The insert 166 can generally extend for a length that enables sleeve 108b to be inserted into and visibly aligned within the throughbore 164 of the cannula 158b. The insert 166 can define threads 167 to engage the stop 168.

The stop 168 can extend over the insert 166 at a specified position to provide a safety stop for the drill bit 110b. For example, the stop 168 can extend over the insert 166 such that connector 116 of the sleeve 108b can contact the stop 168 to prevent the continued forward movement of the sleeve 108, and thus, the drill bit 110b. The stop 168 can include an actuator 172 and a housing 174.

The actuator 172 can include threads 176 that can engage the threads 167 defined in the insert 166 of the cannula 158. The actuator 172 can include a biasing element, such as a spring (not specifically shown) to bias the threadeds 176 between a locked position and an unlocked position. In the locked position, the threads 176 can engage the threads 167 to prevent the movement of the stop 168. In the unlocked position, the threads 176 can be released from the threads 167 of the insert 166 so that the stop 168 can be moved relative to the insert 166 to enable the user 39 to select a desired depth for the drill bit 110b to traverse within the anatomy. Typically, depths can be printed or formed on the exterior of the cannula 158b (not shown), and the user 39 can move the stop 168 to the desired depth the user 39 wishes to traverse with the drill bit 110b. Thus, the stop 168 can ensure that the user 39 drills to a selected depth within the anatomy of the patient 12.

The housing 174 can retain the actuator 172. The housing 174 can protrude above the insert 166. Generally, the housing 174 can be sized such that a portion of the housing 174 can contact the connector 116 of the sleeve 108b to prevent the advancement of the drill bit 110b beyond the depth set by the actuator 172. It should be noted that although the stop 168 is described herein as including a distinct actuator 172 and housing 174, the stop 168 could comprise a one-piece assembly, or any other device capable of contacting the connector 116 of the sleeve 108b to prevent the further advancement of the drill bit 110b.

The distal end 162 of the cannula 158b can include a tip 178. The tip 178 can be coupled to the proximal end 160 of the cannula 158, via the tube 163, however, the tip 178 and tube 163 could be integrally formed with the proximal end 160 of the cannula 158, if desired. The tip 178 can be tapered to facilitate the passing of the cannula 158 into an anatomy of the patient 12. The tip 178 can also include barbs or teeth to facilitate the penetration of the cannula 158b into the anatomy. The throughbore 164 can be defined through the cannula 158b for receipt of the sleeve 108b and drill bit 110b therethrough.

In order to assemble the drill 104b, the sleeve 108b can be slid over the drill bit 110b, such that the electromagnetic coils 142 can be adjacent to the distal end 140 of the sleeve 108b when the drill bit 110b is inserted into the sleeve 108b. Then, the user 39 can compress the actuator 172 of the stop 168 to move the stop 168 into a position that corresponds with the desired depth for the drill bit 110b to traverse. The user 39 can release the actuator 172 to return the stop 168 to the locked position. The user 39 can next insert the sleeve 108b and the drill bit 110b into the slot 165 of the cannula 158b of the drill guide 106b. Then, the user 39 can position the tip 178 of the cannula 158b into the selected area of the anatomy, and can actuate the drill 104b to advance the drill bit 110b into the anatomy of the patient 12. The position and trajectory of the drill bit 110b can be tracked by the tracking system 44, as will be discussed herein.

Referring now to FIGS. 6-10, additional exemplary instruments 52 are shown for use with the navigation system 10. In this example, the instruments 52 can be configured to be used with the electromagnetic tracking system 44, however, the instruments 52 could be configured to be used with the optical tracking system 44b or a hybrid tracking system (not shown). As the instruments 52 can be substantially similar to the instruments discussed with regard to FIGS. 2-5, the same reference numerals will be used to discuss the same or similar components. With continuing reference to FIGS. 6-10, the instruments 52 can include a drill 104c (FIG. 6), a drill guide 106c (FIG. 6-10) and a trocar 298 (FIG. 10) that can be used with the drill guide 106c. The drill 104c can comprise a sleeve 108c and a drill bit 110c.

With reference to FIG. 7, the sleeve 108c can include a connector 116c, a controller 130c, a spring 118c, the bushing 120 and the tracking device 58c, each of which can be coupled to the body 122 of the sleeve 108c. As the body 122 and tracking device 58 can be substantially similar to the body 122 and tracking device 58 discussed with regard to FIGS. 3-5, the body 122 and tracking device 58 will not be discussed in great detail herein. With reference to FIG. 8A, the connector 116c can be coupled to the drill guide 106c, adjacent to the proximal end 124 of the body 122 of the sleeve 108c. With additional reference to FIG. 7, the connector 116c can include a throughbore 300 and a threaded flange 302. The throughbore 300 can be threaded, and can enable the trocar 298 to be inserted through the sleeve 108c, as will be discussed with regard to FIG. 10. The throughbore 300 can also have a diameter that is sized such that the drill bit 110c can pass therethrough, as shown in FIG. 8B.

Figure 8:
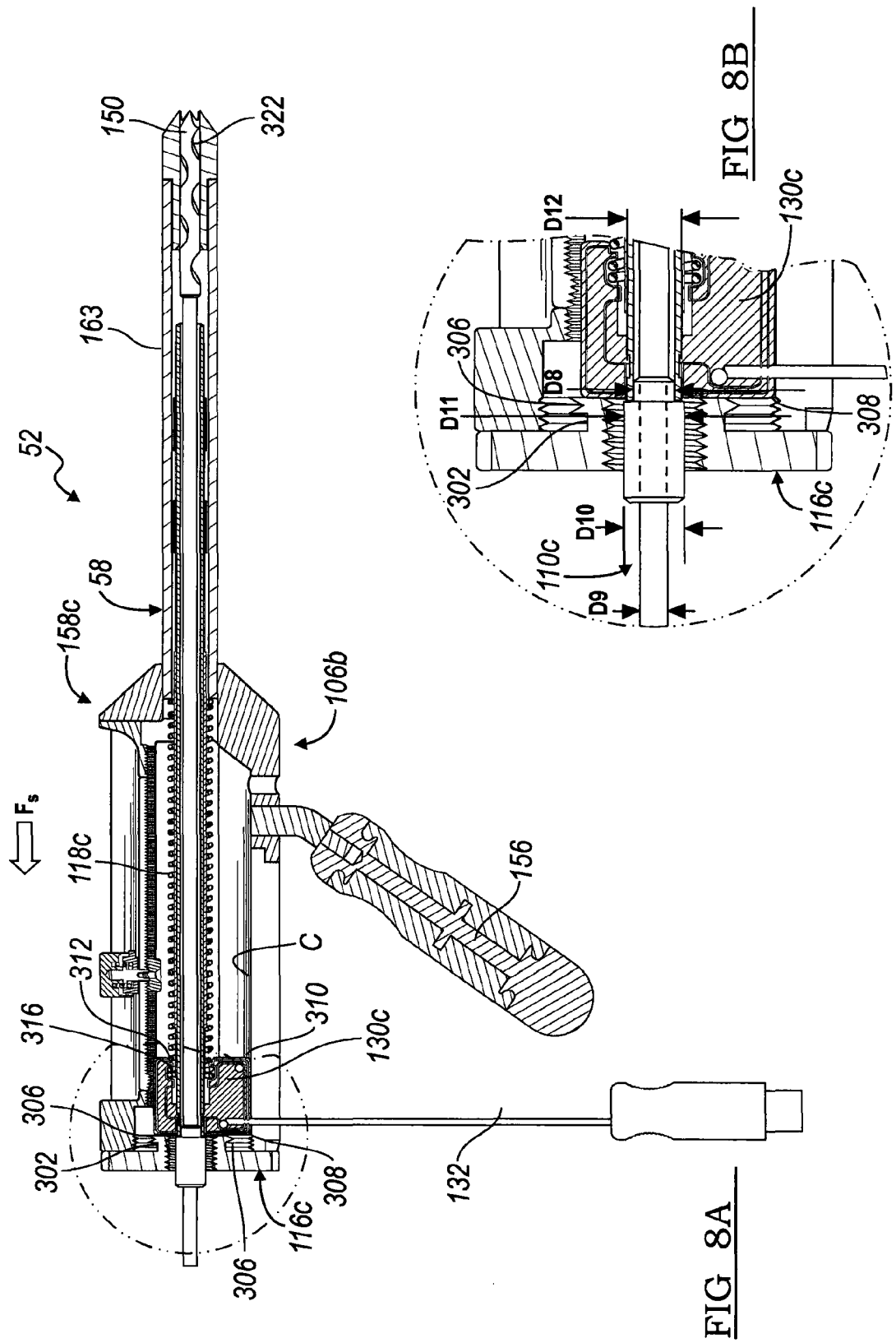

With reference to FIGS. 7-8B, the threaded flange 302 can couple the sleeve 108c to the drill guide 106c by threadably engaging mating threads 306 formed on the drill guide 110c. It should be noted, however, that any fixation means could be used to secure the sleeve 108c within the drill guide 106c, such as threaded fasteners and the like. The engagement of the threaded flange 302 with the drill guide 106c can also retain the controller 130c within the drill guide 106c, and can compress the spring 118c.

The controller 130c can be coupled to the sleeve 108c, and can be slideably retained within the drill guide 110c by the connector 116c. In this regard, the connector 116c can retain the controller 130c within a channel C defined in the drill guide 110c to enable the controller 130c to move relative to the drill guide 110c to enable the tracking system 44 to track the distal end of the instrument 52, as will be discussed. As the controller 130c can be substantially similar to the controller 130 discussed with regard to FIGS. 3-5, only the differences between the controller 130 and the controller 130c will be discussed herein. The controller 130c can have a proximal end 308, a distal end 310 and can define a bore 312. The proximal end 308 can contact the connector 116c when the connector 116c is coupled to the drill guide 106c (FIGS. 8A, 8B). The distal end 310 can contact the stop 168 of the drill guide 110c to control the advancement of the distal end of the instrument 52 relative to the anatomy of the patient 12, as will be discussed with regard to FIG. 9.

The controller 130c can receive the current from the tracking device 58, and can transmit a signal indicative of the current of the tracking device 58 to the navigation probe interface 50 via at least the cable 132. Although not shown, the cable 132a can be used to transmit the signal from the tracking device 58 to the controller 130c, as discussed with regard to the controller 130 of FIGS. 3-5. It will be understood, however, that although a wired connection is illustrated herein, any suitable technique could be used to transmit the current from the tracking device 58 to the controller 130c and the navigation probe interface 50, such as a wireless connection.

The spring 118c can be coupled to the controller 130c via the spring retainer 316. The spring 118c can also contact and bias against the tube 163 of the drill guide 106c to enable the compression of the spring 118c (FIG. 8A). As the spring 118c can be any suitable biasing member, the spring 118c will not be discussed in greater detail herein. Briefly, however, the compression of the spring 118c can provide a spring force Fs that prevents the undesired movement of the tracking device 58. Generally, the spring 118c can be sized such that when the connector 116c is engaged with the drill guide 110c, as shown in FIG. 8A, the spring 118c is compressed to apply a spring force Fs against the distal end 310 of the controller 130c.

With reference to FIG. 7, the drill bit 110c can include the tip 150 and a body 152c. The tip 150 can be pointed such that the tip 150 can engage the anatomy of the patient 12 to remove a selected portion of the anatomy. The body 152c can have a proximal end 320 and a distal end 322. The tip 150 can be disposed at the distal end 322 of the body 152c. With reference to FIGS. 7-8B, the body 152c can include a first annular flange 324 and a second annular flange 326, each disposed at the proximal end 320 of the body 152c. The first annular flange 324 can have a diameter D8 that is substantially equal to an inner diameter D9 of the sleeve 108c so that the first annular flange 324 can rotatably couple the drill bit 110c to the sleeve 108c (FIG. 8B). The second annular flange 326 can have a diameter D10 that is at least greater than the diameter D9 of the sleeve 108c, but less than a diameter D11 of the throughbore 300 of the connector 116c, and generally about equal to an outer diameter D12 of the sleeve 108c, such that the second annular flange 326 can contact the proximal end 124 of the sleeve 108c. The contact between the second annular flange 326 and the sleeve 108c can cause the sleeve 108c, and thus, the controller 130c and the tracking device 58 to move relative to the drill guide 106c upon the advancement of the drill bit 110c, as will be discussed herein.

With reference to FIGS. 6-10, as the drill guide 106c can comprise any suitable guide that enables the user 39 to direct the motion of the drill bit 110c within the anatomy, and can be substantially similar to the drill guide 106c discussed with regard to FIGS. 3-5, only the differences between the drill guide 106 of FIGS. 3-5 and the drill guide 106c will be discussed herein, and the same reference numerals will be used to refer to similar components. The drill guide 106c can comprise a cannula 158c. The cannula 158c can be illustrated as a two-piece component including a first housing 340 and a second housing 342, however, the cannula 158c can be integrally formed with a one-piece construction. The first housing 340 can be coupled to the second housing 342 via one or more mechanical fasteners, however, any suitable fastening system, such as welding, bonding adhesives, rivets, etc., could be employed. The cannula 158c can include the mating threads 306 and the channel C at the proximal end 160. The mating threads 306 can enable the connector 116c to be coupled to the drill guide 106c. The channel C can define a path for the linear movement of the controller 130c. The channel C can comprise a slot formed in the cannula 158c, as shown in FIGS. 7 and 8A, but could comprise any suitable means for controlling the linear movement of the controller 130c, such as a rib, etc.

With reference to FIG. 10, the trocar 298 can be inserted into the throughbore 300 of the connector 116c to prepare the anatomy of the patient 12 for receipt of the drill bit 110c. The trocar 298 can include a handle 350 and a body 352. The handle 350 can releasably couple the trocar 298 to the drill guide 106c. In this regard, the handle 350 can comprise a graspable portion 354 that can include a threaded receiver 356. The graspable portion 354 can be employed to manipulate the trocar 298 into engagement with the drill guide 106c, by maneuvering threads 358 on the threaded receiver 356 into engagement with the threads flange 302 formed on the throughbore 300. The graspable portion 354 can also include a contact surface 354a that can contact the connector 116c of the drill guide 104c when the threads 358 are engaged with the connector 116c.

The threaded receiver 356 can include the threads 358, which can be formed opposite a receiver aperture 360. The threaded receiver 356 can have a diameter D12 that can be sized such that the threads 358 can meshingly engage the threads flange 302 of the throughbore 300. The receiver aperture 360 can couple the body 352 to the graspable portion 354 of the trocar 298. The receiver aperture 360 can be sized such that the receiver aperture 360 can contact the controller 130c, and thus, can cause the controller 130c to advance within the drill guide 106c until the contact surface 354a of the graspable portion 354 contacts the connector 116c. Therefore, the advancement of the controller 130c can correspond to an advancement of a tip 364 of the body 352 of the trocar 298 beyond the distal end 162 of the cannula 158c.

The body 352 of the trocar 298 can include a proximal end 362 and a distal end 368. The proximal end 362 can be configured to mate with the receiver aperture 360 to fixedly couple the body 352 to the handle 350 of the trocar 298. The proximal end 362 can include an annular flange 367. The annular flange 367 can have a diameter that is at least greater than the diameter D9 of the sleeve 108c, but at least is smaller than the diameter D11 of the throughbore 300 of the connector 116c (FIG. 8B). The proximal end 362 can be press fit into the receiver aperture 360, for example, however, any appropriate fixation technique could be used to couple the body 352 to the handle 350, such as a mechanical fastener, bonding, welding, mating threads, etc. The distal end 368 can include the tip 364. The tip 364 can extend from the distal end 162 of the drill guide 106c and can be used to prepare the anatomy for receipt of the drill bit 110. The tip 364 can include multiple teeth 366 for engagement with the anatomy, as is generally known. The tip 364 of the trocar 298 can be configured to engage the anatomy to bore through the skin and tissue of the patient 12 so that when the trocar 298 is removed, the drill 104c can be positioned adjacent to the bone of the patient 12.

In order to assemble the drill 104c, the sleeve 108c and the spring 118c can be coupled the controller 130c. Then, the sleeve 108c, spring 118c and the controller 130c can be slid into the channel C of the drill guide 106c. With the controller 130c inserted into the channel C, the connector 116c can be threaded into engagement with the mating threads 306 of the drill guide 110c such that the spring 118c is compressed. Further, the user 39 can compress the actuator 172 of the stop 168 to move the stop 168 into a position that corresponds with the desired depth for the drill bit 110 to traverse. The user 39 can release the actuator 172 to return the stop 168 to the locked position.

With the connector 116c coupled to the drill guide 106c and the desired depth set by the user 39, the user 39 can optionally couple the trocar 298 to the drill guide 106c. In order to couple the trocar 298 to the drill guide 106c, the body 352 of the trocar 298 can be inserted such that the threads 358 of the handle 350 can engage the threads 306 formed on the throughbore 300 (FIG. 9). Then, the handle 350 can be rotated until the contact surface 356a abuts the connector 116c. This rotation of the handle 350 can gradually advance the tip 364 of the trocar 298 beyond the end of the drill guide 106c to prepare the anatomy for receipt of the drill bit 110c. Given the diameter of the receiver aperture 360, as the tip 364 is advanced beyond the drill guide 106c, the receiver aperture 360 can apply a force to the proximal end 308 of the controller 130c that can overcome the spring force Fs to enable the controller 130c to move relative to the drill guide 106c in the channel C. The relative movement of the controller 130c can be substantially equivalent to a distance traveled by the tip 364 relative to the end of drill guide 106c. Thus, based on the movement of the controller 130c, the position of the distal end of the instrument 52, in this example the tip 364 of the trocar 298, can be tracked by the tracking system 44, as will be discussed herein. The trocar 298 can be removed from the drill guide 106c by unscrewing the handle 350 from the connector 116c of the drill guide 106c.

With the trocar 298 removed from the drill guide 106c, the drill bit 110c can be inserted into the drill guide 106c. Generally, the drill bit 110c can be inserted until the first annular flange 324 is disposed within the sleeve 108c, with the second annular flange 326 just contacting the proximal end 308 of the controller 130c, without encountering the spring force Fs, as shown in FIG. 8A. As the user 39 advances the drill bit 110c further, the second annular flange 326 can contact the proximal end 308 of the controller 130c, which can require the user 39 to apply a force F to the drill 104, and thus, the drill bit 110c, to overcome the spring force Fs in order to advance the drill bit 110c within the anatomy of the patient 12, as shown in FIG. 9. The advancement of the drill bit 110c within the anatomy can cause the controller 130c to move relative to the drill guide 106c a distance $D_c$, which can be about equivalent to the distance $D_t$ traveled by the drill bit 110c beyond the distal end 162 of the cannula 158c (FIGS. 6 and 9). Thus, the movement of the controller 130c within the channel C can enable the tracking system 44 to track the end of the instrument 52, in this case the tip 150 of the drill bit 110c, as will be discussed herein.

With reference now to FIG. 11, a simplified block diagram schematically illustrates an exemplary navigation system 10 for implementing the control module 101. The navigation system 10 can include the tracking system 44, the tracking devices 58, a navigation control module 200 and the display 36. The tracking system 44 can comprise an electromagnetic tracking system 44 or an optical tracking system 44b, and will generally be referred to as tracking system 44. The tracking system 44 can receive start-up data 202 from the navigation control module 200. Based on the start-up data 202, the tracking system 44 can set activation signal data 204 that can activate the tracking device 58. The tracking system 44 can also set tracking data 208 to the navigation control module 200, as will be discussed. The tracking data 208 can include data regarding the location of the tip or distal end 162 of the instrument 52, which can be determined from the signals received from the controller 130 of the tracking device 58 for the instrument 52.

When the tracking device 58 is activated, the controller 130 can transmit sensor data 210 indicative of the signal generated by the tracking device 58 over the cable 132a to the tracking system 44. Based on the sensor data 210 received by the tracking system 44, the tracking system 44 can generate and set the tracking data 208 for the navigation control module 200, as will be discussed further herein.

The navigation control module 200 can receive the tracking data 208 from the tracking system 44 as input. The navigation control module 200 can also receive patient image data 100 as input. The patient image data 100 can comprise images of the anatomy of the patient 12 obtained from a pre- or intra-operative imaging device, such as the images obtained by the imaging device 14. Based on the tracking data 208 and the patient image data 100, the navigation control module 200 can generate image data 102 for display on the display 36. The image data 102 can comprise the patient image data 100 superimposed with an icon 103 of the instrument 52, as shown in FIG. 1. The icon 103 can provide a graphical representation of the position and trajectory of the distal end of the instrument 52 (i.e., distal end 162 of the cannula 158 or tip 150 of the drill bit 110) relative to the anatomy of the patient 12. In addition, the icon 103 can illustrate a starting point of the drill bit 110, (i.e., an "X" adjacent to a bone in the anatomy) and can illustrate the trajectory of the drill bit 110 through the anatomy, (i.e., dashes from the "X"). A current location of the drill bit 110 can also be displayed by the icon 103 (i.e., an "O" at the end of the dashes). It should be understood, however, that any suitable symbol, indicia or the like could be employed to graphically represent the location and/or trajectory of the drill bit 110 relative to the anatomy.

With reference now to FIG. 12, a dataflow diagram illustrates an exemplary control system that can be embedded within the control module 101. Various embodiments of the tracking control system according to the present disclosure can include any number of sub-modules embedded within the control module 101. The sub-modules shown may be combined and/or further partitioned to similarly determine the position of the drill bit 110 based on the signal generated by the tracking device 58. Inputs to the system can be received from the C-arm 16, or even received from other control modules (not shown) within the navigation system 10, and/or determined by other sub-modules (not shown) within the control module 101 (not shown). In various embodiments, the control module 101 includes the tracking system 44 that can implement a tracking control module 220, and the workstation 34 that can implement the navigation control module 200. It should be noted that the tracking control module 220 can be implemented by the tracking system 44 and the navigation control module 200 can be implemented on the workstation 34, however, both of the tracking control module 220 and the navigation control module 200 could be implemented on the workstation 34, if desired.

The tracking control module 220 can receive as input the start-up data 202 from the navigation control module 200 and sensor data 210 from the tracking device 58. Upon receipt of the start-up data 202, the tracking control module 220 can output the activation signal data 204 for the tracking device 58. Upon receipt of the sensor data 210, the tracking control module 220 can set the tracking data 208 for the navigation control module 200.

The navigation control module 200 can receive as input the tracking data 208 and patient image data 100. As discussed, the tracking data 208 can comprise the distal end of the instrument 52 in patient space. Based on the tracking data 208, the navigation control module 200 can determine the appropriate patient image data 100 for display on the display 36, and can output both the tracking data 208 and the patient image data 100 as image data 102.

With reference now to FIG. 13, a process flow diagram illustrates an exemplary method performed by the tracking control module 220. At decision block 250, the method can determine if start-up data 202 has been received from the navigation control module 200. If no start-up data 202 has been received, then the method loops to decision block 250 until start-up data 202 is received. If start-up data 202 is received, then the method goes to block 252. At block 252, the tracking system 44 can generate the activation signal data 204. Then, at decision block 254 the method can determine if the sensor data 210 has been received. If the sensor data 210 has been received, then the method goes to block 256. Otherwise, the method loops to decision block 254 until the sensor data 210 is received.

At block 256, the method can compute the location and position of the distal end of the instrument 52 in patient space based on the sensor data 210. In this regard, the sensor data 210 can provide a location of the tracking device 58 in patient space. For example, the distal end 162 of the drill guide 106 and the depth of the tip 150 of the drill bit 110 can be determined based on the movement of the tracking device 58 relative to the drill guide 106. At block 258, the method can output the tracking data 208. Then, the method can loop to decision block 250.

In operation, after the drill guide 106 has been assembled, the user 39 can couple the trocar 298 to the drill guide 106c, if desired, or can insert the drill bit 110 into the drill guide 106c. Then, the cable 132 of the tracking device 58c can be coupled to the navigation probe interface 50. The user 39 can use the user input device 38, for example, to instruct the navigation system 10 to activate the tracking system 44. The navigation system 10 can then send the start-up data 202 to the tracking control module 220. On receipt of the start-up data 202, the tracking control module 220 can output the activation signal data 204.

The activation signal data 204 can induce a signal from the tracking device 58. As the signal from the tracking device 58 corresponds to a unique location in the patient space, the tracking system 44 can readily determine the location of the tracking device 58 in the patient space. Thus, as the user 39 manipulates the instrument 52 in the patient space, the tracking device 58 can enable the tracking system 44 to determine the depth or the position of the distal end of the instrument 52, such as the position of the distal end 162 of the cannula 158 or the tip 150 of drill bit 110 during the surgical procedure.

Based on the location or position of the distal end of the instrument 52, the navigation control module 200 can determine the appropriate patient image data 100 that corresponds to the determined location of the end of the instrument 52, such as the distal end 162 of the cannula 158 or the tip 150 of the drill bit 110. The navigation control module 200 can then output the image data 102 that comprises the patient image data 100 with the icon 103 superimposed on the patient image data 100 to the display 36. Thus, the user 39 can be provided with a graphical representation of the trajectory and/or location of the instrument 52, for example, the distal end 162 of the cannula 158 or the tip 150 and/or trajectory of the drill bit 110 of the instrument 52, relative to the anatomy of the patient 12 in patient space.

Therefore, the drill 104 and the drill guide 106 of the present disclosure can provide a user, such as a surgeon, with an accurate representation of the position and trajectory of the distal end of the instrument 52, such as the distal end 162 of the drill guide 106 or the tip 150 of the drill bit 110 within the drill guide 106, during the surgical procedure. The use of a tracking device 58 that can move relative to the instrument 52, in this example, the drill guide 106, can enable an accurate depiction of the depth or position and trajectory of the distal end of the instrument 52. Alternatively, the tracking device 58c in combination with the segments 154 on the drill bit 110b can enable an accurate depiction of the depth or position of the drill bit 110b within the anatomy of the patient 12, and can also provide an accurate representation of the rotational movement or trajectory of the drill bit 110b in the patient space. In addition, the known location of the electromagnetic coils 142 on the sleeve 108 of the drill 104 can update the user 39 regarding the accuracy of the instrument 52. Thus, if the drill guide 106 or drill bit 110 is dropped, bent or otherwise damaged during the procedure, the use of the electromagnetic sensors or coils 142 at a known distance can enable the navigation system 10 to verify the accuracy of the instrument 52 throughout the surgical procedure. Further, any changes in the distance between the electromagnetic coils 142 can be compensated for by the tracking control module 220, if so desired.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. A system comprising:
    a guide instrument that has a first proximal end, a first distal end and defines a first bore, the guide instrument positionable with a handle adjacent to an anatomy;
    a sleeve having a second proximal end, a second distal end and a second bore, the sleeve slideably received within the first bore;
    a drill bit slideably received within the second bore and moveable relative to the sleeve, having a third distal end and an axially extending body composed of a first non-ferrous metal material, the body including at least two distinct segments that are axially separated, wherein the at least two distinct segments composed of a second non-ferrous metal material, the first non-ferrous metal material having a first magnetic permeability different from a second magnetic permeability of the second non-ferrous metal material and the at least two distinct segments include a segment length less than a total length of the body;
    at least one tracking device fixedly coupled about the sleeve; and
    a controller configured to receive a varying signal from the at least one tracking device based at least on the first magnetic permeability different from the second magnetic permeability;
    wherein when the sleeve is in a first position, the at least one tracking device indicates a position of the first distal end of the guide instrument, and when the sleeve is in a second position, the at least one tracking device indicates a position of the third distal end of the drill bit;
    wherein movement of the drill bit relative to and within the second bore of the sleeve and relative to the at least one tracking device acts to change a current induced in the at least one tracking device due to movement of a first distinct segment and a second distinct segment of the at least two distinct segments through the at least one tracking device and to determine a depth of the third distal end;
    wherein the controller receives the varying signal based on the current induced in the at least one tracking device to at least assist in determining at least one of a position or a trajectory of the drill bit.

2. The system of claim 1, further comprising:
    a drill configured to operably engage the drill bit to move the drill bit within the second bore;

wherein the at least one distinct segment of the body of the drill bit further comprises three distinct segments, wherein each of the three distinct segments is spaced apart at the third distal end of the drill bit, each of the three distinct segments having a different permeability to change the current induced by the at least one tracking device and each of the three distinct segments have segments lengths less than the total length of the body.

3. The system of claim 1, further comprising:
a tracking system that tracks the at least one tracking device; and
an imaging device selected from a fluoroscopy device, an O-arm device, a bi-plane fluoroscopy device, an ultrasound device, a computed tomography (CT) device, a multi-slice computed tomography (MSCT) device, a magnetic resonance imaging (MRI) device, a high frequency ultrasound (HFU) device, a positron emission tomography (PET) device, an optical coherence tomography (OCT) device, an intra-vascular ultrasound (IVUS) device, an intra-operative CT device, an intra-operative MRI device and combinations thereof.

4. A method comprising:
positioning a first elongated instrument relative to a second elongated instrument, the first elongated instrument having a first proximal end, a first distal end and a first bore with at least one tracking device positioned around the first bore of the first elongated instrument, the second elongated instrument having a second proximal end and a second distal end;
moving the second elongated instrument within the first bore of the first elongated instrument to vary a signal induced in the at least one tracking device due to a plurality of distinct and separated segments spaced along the length of the second elongated instrument, wherein each distinct and separated segment is formed of a first material that differs from a second material forming the remaining portions of the second elongated instrument, wherein the first material has different magnetic permeability than the second material forming the second elongated instrument;
tracking the at least one tracking device; and
determining, based on the tracking of the at least one tracking device, a location of the first distal end of the first elongated instrument or the second distal end of the second elongated instrument.

5. The method of claim 4, further comprising:
determining, based on the varying of the signal induced in the at least one tracking device, a depth of the second elongated instrument at least relative to the at least one tracking device;
wherein the signal is varied based on the plurality of distinct and separated segments formed of the first material and separated a distance from the second distal end of the second elongated instrument.

6. A method comprising:
positioning a first elongated instrument with a handle relative to a second elongated instrument, the first elongated instrument having a first proximal end and a first distal end and a first bore extending therebetween, the second elongated instrument including a sleeve and a drill bit, the sleeve having a second proximal end, a second distal end, and a second bore with at least one tracking device positioned around the sleeve and the second bore, the drill bit having a third proximal end and a third distal end, the drill bit provided with at least a first segment and a second segment discrete and separated by a distance from the first segment, the first segment and the second segment disposed at fixed and different positions spaced from the third distal end;
moving the drill bit within the second bore of the sleeve to vary an amount of current induced in the at least one tracking device due to positioning at least one of the first segment or the second segment within the at least one tracking device, wherein an amount of current induced is based at least on the first segment and the second segment being formed of a segment material having a first magnetic permeability different than a second magnetic permeability of a drill bit material of the remainder of the drill bit;
and
tracking of at least the third distal end of the drill bit based on varying the current induced in the at least one tracking device with the first segment or the second segment having the first magnetic permeability and second magnetic permeability.

7. The method of claim 6, further comprising:
positioning the at least one tracking device around the sleeve; and
securing the sleeve within the first bore such that the sleeve is biased into a first position, but is able to move relative to the first elongated instrument into a second position.

8. The method of claim 7, further comprising:
determining, based on tracking of the at least one tracking device, the location of the first distal end or the third distal end, comprising:
determining the location of the first distal end if the sleeve is in the first position, and
determining the location of the third distal end if the sleeve has moved relative to the first elongated instrument into the second position.

9. The method of claim 8, further comprising:
providing an image of an anatomy; and
displaying the position of the first distal end, the second distal end or combinations thereof relative to an anatomy on a display.

10. The method of claim 7, further comprising:
positioning the sleeve at a first physical position within the first bore and determining a position with the at least one tracking device of the second distal end of the first elongated instrument; and
positioning the sleeve at a second physical position within the first bore and determining with the at least one tracking device a position of the third distal end of the drill bit.

11. The method of claim 6, further comprising:
placing at least a third segment on the drill bit.

12. The method of claim 11, further comprising:
forming at least one of the first segment, the second segment, or the third segment within the drill bit.

13. The method of claim 6, further comprising:
determining at least a depth of the drill bit based at least on the varied current induced within the at least one first tracking device.

14. The method of claim 6, wherein the segment material of the first segment and the second segment are different.

15. The method of claim 6, further comprising:
determining a location of at least the third distal end based on the varied current induced due to the first segment and the second segment.

16. The method of claim 6, further comprising:
providing at least the first segment separate from the second segment with a different, distinct non-ferrous metal material, wherein at least one of the first segment and the second are adjacent to a distinct non-ferrous metal material; and determining at least one of a position or a trajectory of the drill bit at least with the change in current induced in the at least one tracking device.

17. A system comprising:
a sleeve that has a first proximal end, a first distal end and a first bore;
a guide instrument that has a second proximal end, a second distal end and defines a second bore that is adapted to slideably receive the sleeve, the guide instrument positionable with a handle adjacent to an anatomy;
at least one electromagnetic tracking device coupled to the sleeve, the at least one electromagnetic tracking device moveable relative to the guide instrument; and
a drill bit slideably received within the first bore, the drill bit having a body composed of a first material, the body including at least two distinct segments composed of a second material that is different from the first material;
wherein when the sleeve is at a first physical position within the first bore of the guide instrument, the at least one electromagnetic tracking device indicates a position of the second distal end of the guide instrument;
wherein when the sleeve is at a second physical position within the first bore of the guide instrument, the at least one electromagnetic tracking device indicates a position of the third distal end of the drill bit.

18. The system of claim 17, wherein the second elongated instrument further comprises:
a biasing member coupled to the sleeve and retained within the first bore that applies a force to the sleeve to bias the sleeve in the first position; and
wherein in the second position, the drill bit moves the sleeve relative to the guide instrument and the relative movement between the sleeve and the guide instrument corresponds to a position of the third distal end.

19. The system of claim 17, wherein the at least one electromagnetic tracking device comprises at least one electromagnetic receiver coil positioned about the first bore and the relative movement of the drill bit within the sleeve acts as a core of the at least one electromagnetic receiver coil to vary a signal induced in the at least one electromagnetic coil, wherein a position of the drill bit is determined based on the varied signal induced based on moving the at least two distinct segments composed of the second-material that is different from the first material relative to the at least one electromagnetic receiver coil.

20. The system of claim 17, wherein the at least two distinct segments are axially spaced apart in the drill bit, wherein the at least one electromagnetic tracking device comprises at least one electromagnetic transmitter coil positioned around the first bore and the relative movement of the at least two distinct segments of the drill bit within the sleeve acts as at least two cores to the at least one electromagnetic transmitter coil to vary an electromagnetic field generated by the at least one electromagnetic coil as the first material and the second material move within the at least one electromagnetic transmitter coil, wherein a position of the drill bit is determined due to the varied electromagnetic field generated based on moving the at least two distinct segments composed of the second material that is different from the first material relative to the at least one electromagnetic receiver coil.

21. The system of claim 20, wherein each of the at least two segments is formed of a unique non-ferrous metal material, wherein the position of the drill bit is determined with use of the at least two distinct segments of the unique non-ferrous metal material to result in the change in the varied electromagnetic field generated.

22. The system of claim 17, wherein the first material has a different magnetic permeability than the second material.

23. The system of claim 17, further comprising:
a tracking system that tracks the at least one electromagnetic tracking device; and
an imaging device selected from a fluoroscopy device, an O-arm device, a bi-plane fluoroscopy device, an ultrasound device, a computed tomography (CT) device, a multi-slice computed tomography (MSCT) device, a magnetic resonance imaging (MRI) device, a high frequency ultrasound (HFU) device, a positron emission tomography (PET) device, an optical coherence tomography (OCT) device, an intra-vascular ultrasound (IVUS) device, an intra-operative CT device, an intra-operative MRI device and combinations thereof.

* * * * *